United States Patent
Fujii et al.

[19]

[11] Patent Number: 6,143,060
[45] Date of Patent: Nov. 7, 2000

[54] TRIAZINE DERIVATIVES AND RECORDING MATERIALS PREPARED THEREFROM

[75] Inventors: Hiroshi Fujii; Tomoya Hidaka; Shinichi Sato; Izuo Aoki, all of Ichihara, Japan

[73] Assignee: Nippon Soda Co., Ltd., Tokyo, Japan

[21] Appl. No.: 09/068,187

[22] PCT Filed: Oct. 30, 1996

[86] PCT No.: PCT/JP96/03176

§ 371 Date: May 1, 1998

§ 102(e) Date: May 1, 1998

[87] PCT Pub. No.: WO97/16431

PCT Pub. Date: May 9, 1997

[30] Foreign Application Priority Data

Nov. 1, 1995 [JP] Japan ..................................... 7-308409
Dec. 5, 1995 [JP] Japan ..................................... 7-344628
Mar. 19, 1996 [JP] Japan ..................................... 8-090446
Mar. 22, 1996 [JP] Japan ..................................... 8-093319

[51] Int. Cl.$^7$ ..................... C09D 11/02; C07D 251/30
[52] U.S. Cl. ..................... 106/31.47; 106/31.17; 106/31.18; 544/218; 544/219
[58] Field of Search ............... 106/31.47, 31.17, 106/31.18; 544/218, 219

[56] References Cited

U.S. PATENT DOCUMENTS

| | | | |
|---|---|---|---|
| 4,446,209 | 5/1984 | Iwakura et al. | 503/216 |
| 4,453,744 | 6/1984 | Wurmli et al. | 503/216 |
| 4,568,766 | 2/1986 | Yahagi et al. | 568/33 |
| 4,605,940 | 8/1986 | Kinishi et al. | 503/209 |
| 4,616,239 | 10/1986 | Yahagi et al. | 503/201 |
| 5,314,786 | 5/1994 | Roeschert et al. | 430/270 |
| 5,463,133 | 10/1995 | Sato et al. | 568/33 |
| 5,489,499 | 2/1996 | Yumoto | 430/281.1 |
| 5,489,503 | 2/1996 | Toan | 430/507 |
| 5,538,840 | 7/1996 | Van Toan | 430/5.2 |

FOREIGN PATENT DOCUMENTS

| | | |
|---|---|---|
| 58/020493 | 2/1983 | Japan . |
| 58-132593 | 8/1983 | Japan . |
| 63-43918 | 2/1988 | Japan . |
| 63-502511 | 9/1988 | Japan . |
| 5-310714 | 11/1993 | Japan . |
| 8-234364 | 11/1993 | Japan . |
| 6-211813 | 8/1994 | Japan . |
| 7-196632 | 8/1995 | Japan . |
| WO93/06074 | 4/1993 | WIPO . |

OTHER PUBLICATIONS

English Translation of the PCT International Preliminary Examination Report for International application No. PCT/JP 96/03176, Oct. 30, 1996.

*Primary Examiner*—Helene Klemanski
*Attorney, Agent, or Firm*—Joseph C. Mason, Jr.; Dennis G. LaPointe; Mason & Associates, PA

[57] ABSTRACT

Triazine derivatives of general formula (I); and recording materials excellent in the storage stability of developed images, particularly the resistance thereof to plasticizers.

6 Claims, No Drawings

TRIAZINE DERIVATIVES AND RECORDING MATERIALS PREPARED THEREFROM

TECHNICAL FIELD

The present invention relates to novel triazine derivatives and recording materials which contain such derivatives and excel in stability of the conservation of a colored image.

BACKGROUND ART

The recording materials which utilize the coloration caused by the reaction between a coloring dye and a developer allow recording to be attained quickly by a relatively simple apparatus without requiring complicated processes such as, for example, development and fixing. Owing to this advantage, they have been widely used as a thermal printing paper for recording the output of a device such as, for example, a facsimile system or a printer and as a pressure-sensitive copying paper for simultaneously copying a plurality of sheets such as in account slips at a time.

These recording materials are required to generate a color quickly, preserve the whiteness of an uncolored part (hereinafter referred to as "background"), and abound in fastness of a colored image and the background thereof. In recent years, they have come to find utility in large quantities in the field of recorded images such as, for example, labels for which reliability forms an important consideration. Thus, the desirability of providing a recording material possessed of a colored image rich in lasting stability to withstand a plasticizer and oil contained in organic high polymer materials which are used in packages has been finding enthusiastic public recognition. With a view to solving this problem, therefore, various studies have been made for the development of various auxiliaries such as conservatives, let alone coloring dyes and developers. None of the outcomes of these studies, however, have been found to be fully satisfactory.

As close equivalents for the compounds of this invention, diphenyl sulfone derivatives may be cited. These have been known as a developer for use in recording materials. The diphenyl sulfone derivatives which have an alkoxy group or aralkyloxy group as one moiety and a hydroxy group as the other moiety have been proposed in JP-A-57-210,886, JP-A-58-20,493, JP-A-58-82,788, JP-58-132,593, JP-A-60-13,852, and IP-A-W084/02882.

None of them, however, deserve to be called fully satisfactory in terms of stability of the conservation of image mentioned above.

Recently, as means to improve the capacity for conservation under discussion, numerous inventions relating to recording materials which contain the novolak type epoxy resin or the epoxy group of a glycidyl compound have been filed for patent. The present patent applicant himself has filed inventions which relate to 4-hydroxy-4'-(2-methyl glycidyloxy) diphenyl sulfone (IP-A-WO93/06074) and phenetyl alcohol derivatives (IP-A-WO94/07832). These inventions are not yet fully satisfactory for the sake of reduction to practice in terms of cleanliness of background and stability of conservation.

The recording materials, therefore, remain yet to be improved in stability of the conservation of a colored image and, particularly in recent years, in resistance to the plasticizer. It is an object of this invention to provide a recording material which excels in stability of the conservation of a colored image for the purpose of solving the problem in question.

DISCLOSURE OF THE INVENTION

This invention is directed to a triazine derivative represented by the general formula (I)

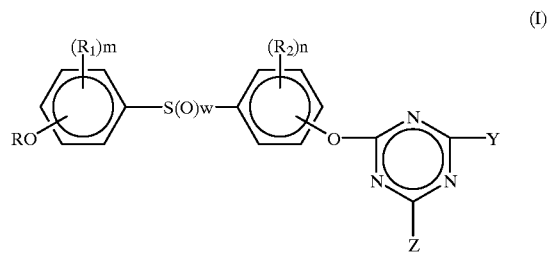

wherein R represents a hydrogen atom or a $C_1$–$C_4$ alkyl group, $R_1$ and $R_2$, which may be the same or different, each represent a hydroxyl group, a halogen atom, a $C_1$–$C_6$ alkyl group, or a $C_2$–$C_4$ alkenyl group, n and m each represent an integer of 0–4, providing that where the integer is not less than 2, $R_1$ and $R_2$ may be different, w represents 0, 1, or 2, Y and Z, which may be the same or different, each represent

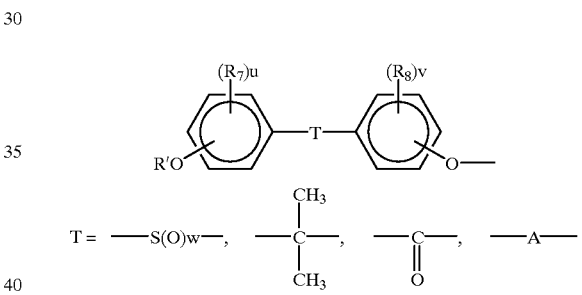

(wherein R' represents a hydrogen atom or a $C_1$–$C_4$ alkyl group, $R_7$ and $R_8$, which may be same or different, each represent a hydroxyl group, a halogen atom, a $C_1$–$C_6$ alkyl group, a $C_2$–$C_4$ alkenyl group, u and v each represent an integer of 0–4, providing that where the integer is not less than 2, $R_7$ and $R_8$ may be different, w represent 0, 1, or 2, and A represents a $C_2$–$C_8$ alkylene group possessing an ether bond), or a halogen atom, a hydroxyl group, a hydrogen atom, a $C_1$–$C_6$ alkoxy group, a $C_1$–$C_6$ alkylthio group, an alkoxy group possessing an ether bond, an alkylthio group possessing an ether bond, an alkoxy group possessing a thioether bond, an alkylthio group possessing a thioether bond, a hydroxyalkoxy group, a hydroxyalkylthio group, a primary or secondary $C_1$–$C_6$ alkylamino group, a primary or secondary $C_1$–$C_6$ hydroxyalkylamino group, an aryloxy group optionally substituted with a hydroxyl group, a $C_1$–$C_4$ alkyl group, or a halogen atom, an arylthio group optionally substituted with a hydroxyl group, a $C_1$–$C_4$ alkyl group, or a halogen atom, an arylamino group optionally substituted with a hydroxyl group, a $C_1$–$C_4$ alkyl group, or a halogen atom, or an aralkyloxy group optionally substituted with a hydroxyl group, a $C_1$–$C_4$ alkyl group, or a halogen atom] and more particularly to a triazine derivative represented by the general formula (II)

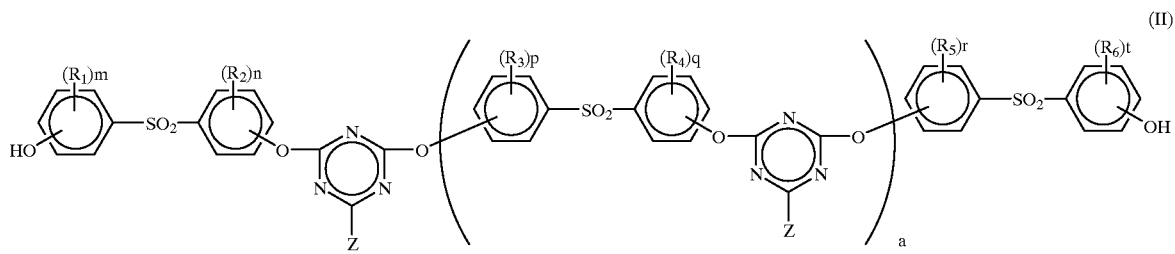

[wherein $R_1$–$R_6$, which may be the same or different, each represent a hydroxyl group, a halogen atom, a $C_1$–$C_6$ alkyl group, a $C_2$–$C_4$ alkenyl group, m, n, p, q, r, and t each represent an integer of 0–4, providing that where the integer is not less than 2, $R_1$–$R_6$ may be different from one another, a represents an integer of 0–10, Z represents

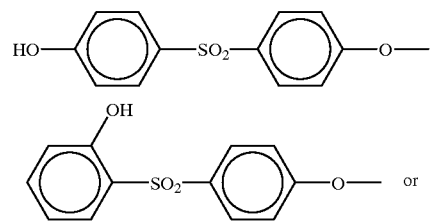

(wherein $R_7$ and $R_8$, which may be the same or different, each represent a hydroxyl group, a halogen atom, a $C_1$–$C_6$ alkyl group, or a $C_2$–$C_4$ alkenyl group, and u and v each represent an integer of 0–4, providing that where the integer is not less than 2, $R_7$ and $R_8$ may be different from each other) or a halogen atom, a hydroxyl group, a hydrogen atom, a $C_1$–$C_6$ alkoxy group, a $C_1$–$C_6$ alkylthio group, an alkoxy group possessing an ether bond, an alkylthio group possessing an ether bond, an alkoxy group possessing a thioether bond, an alkylthio group possessing a thioether bond, a hydroxyalkoxy group, a hydroxyalkylthio group, a primary or secondary $C_1$–$C_6$ alkylamino group, a primary or secondary $C_1$–$C_6$ hydroxyalkylamino group, an aryloxy group optionally substituted with a hydroxyl group, a $C_1$–$C_4$ alkyl group, or a halogen atom, an arylthio group optionally substituted with a hydroxyl group, a $C_1$–$C_4$ alkyl group, or a halogen atom, an arylamino group optionally substituted with a hydroxyl group, a $C_1$–$C_4$ alkyl group, or a halogen atom, or an aralkyloxy group optionally substituted with a hydroxyl group, a $C_1$–$C_4$ alkyl group, or a halogen atom].

This invention is further directed to a composition characterized by containing two or more triazine derivatives represented by the general formula (II)

[wherein $R_1$–$R_6$, m, n, p, q, r, t, a, and Z have the same meanings as mentioned above].

The triazine derivatives of this invention have a triazine skeleton and one S-containing diphenyl compound bound thereto as essential moieties for their structures.

As concrete examples of the substituents, $R_1$–$R_2$, of the S-containing diphenyl group, as one of the essential moieties, a hydroxyl group, halogen atoms such as chlorine, bromine, fluorine, and iodine, $C_1$–$C_6$ alkyl groups such as methyl group, ethyl group, n-propyl group, isopropyl group, n-butyl group, sec-butyl group, tert-butyl group, n-pentyl group, isopentyl group, neopentyl group, tert-pentyl group, n-hexyl group, isohexyl group, 1-methylpentyl group, and 2-methylpentyl group, and $C_2$–$C_4$ alkenyl groups such as vinyl group, allyl group, isopropenyl group, 1-propenyl group, 2-butenyl group, 3-butenyl group, 1,3-butane dienyl group, and 2-methyl-2-propenyl group may be cited. R represents a hydrogen atom or a $C_1$–$C_4$ alkyl group such as methyl group, ethyl group, n-propyl group, isopropyl group, n-butyl group, sec-butyl group, or tert-butyl group.

As concrete examples of the S-containing diphenyl group, which is one of the essential moieties, the following typical compounds may be cited.

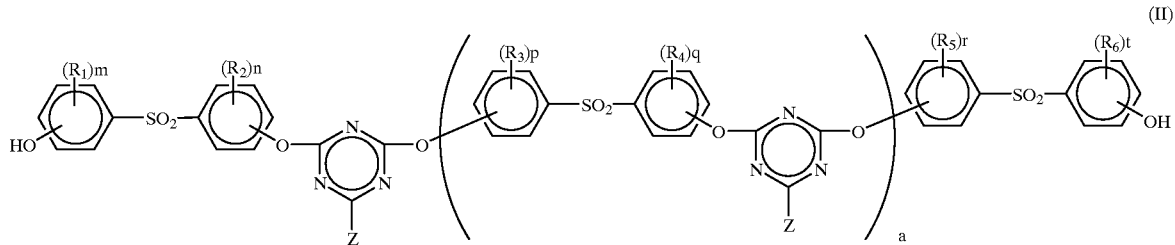

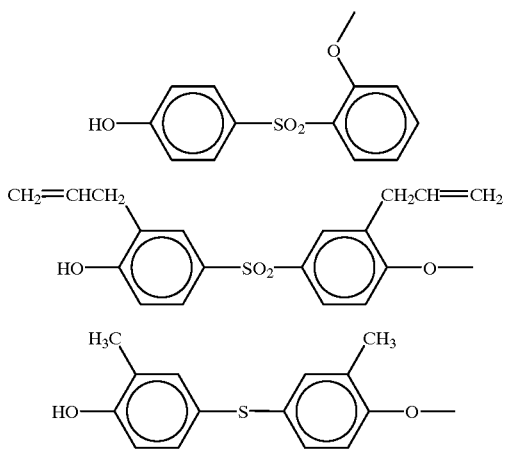

The following groups may be cited as concrete examples of Y and Z.

group, ethyl group, n-propyl group, isopropyl group, n-butyl group, sec-butyl group, and tert-butyl group may be cited. As concrete examples of the substituents, $R_7$ and $R_8$, hydroxyl group, halogen atoms such as chlorine, bromine, fluorine, and iodine, $C_1$–$C_6$ alkyl groups such as methyl group, ethyl group, n-propyl group, isopropyl group, n-butyl group, sec-butyl group, tert-butyl group, n-pentyl group, isopentyl group, neopentyl group, tert-pentyl group, n-hexyl group, isohexyl group, 1-methylpentyl group, and 2-methylpentyl group, and $C_2$–$C_4$ alkenyl groups such as vinyl group, allyl group, isopropenyl group, 1-propenyl group, 2-butenyl group, 3-butenyl group, 1,3-butane dienyl group, and 2-methyl-2-propenyl group may be cited. As concrete examples of A, $C_2$–$C_8$ alkylene groups possessing an ether bond such as ethylene oxyethylene group, tetramethylene oxytetramethylene group, ethylene oxyethylene oxyethylene group, and ethylene oxymethylene oxyethylene group may be cited.

When diphenyl compounds are used for Y and Z, the general formula (I) is transformed into the general formula (III) or (IV).

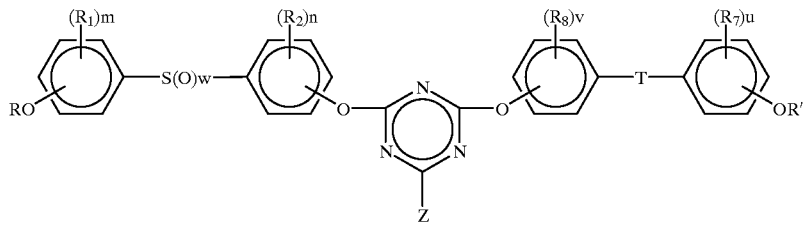
(III)

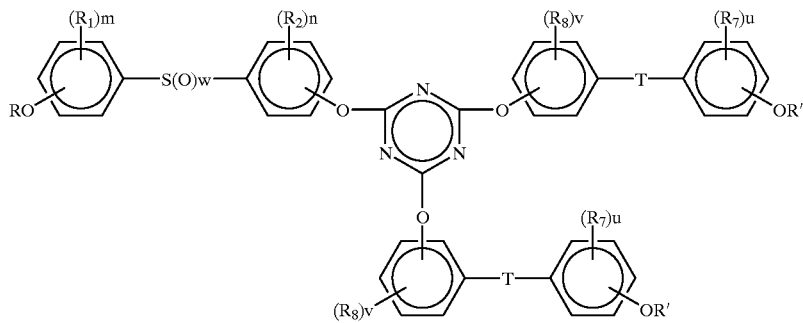
(IV)

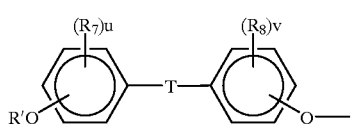

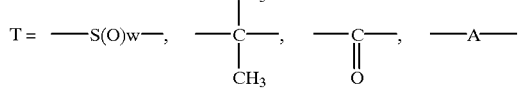

As concrete examples of the substituent, R', shown above, a hydrogen atom and $C_1$–$C_4$ alkyl groups such as methyl The S-containing diphenyl compounds, as the essential moiety mentioned above, can be also used preferably for Y and Z.

Particularly, from the synthetic point of view, the compounds of the general formulas (V) and (VI) prove to be convenient.

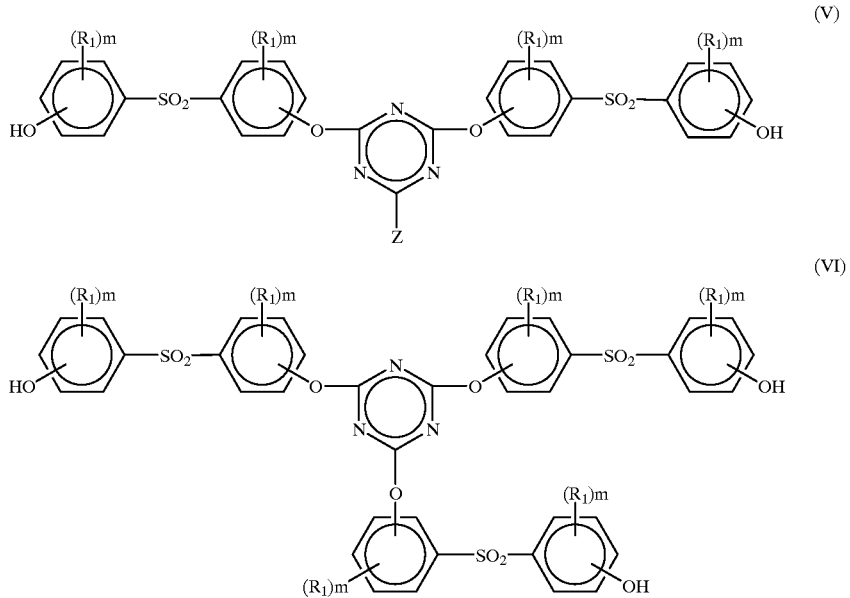

As concrete examples of Y and Z, a hydrogen atom, a hydroxyl group, halogens such as chlorine, bromide, fluorine, and iodine, $C_1$–$C_6$ alkoxy groups such as methoxy, ethoxy, n-propoxy, iso-propoxy, n-butoxy, sec-butoxy, tert-butoxy, n-pentyloxy, iso-pentyloxy, neopentyloxy, tert-pentyloxy, n-hexyloxy, isohexyloxy, tert-pentyloxy, n-hexyloxy, isohexyloxy, 1-methylpentyloxy, and 2-methylpentyloxy group, $C_1$–$C_6$ alkylthio groups such as methylthio, ethylthio, n-propylthio, isopropylthio, n-butylthio, sec-butylthio, tert-butylthio, n-pentylthio, isopentylthio, neopentylthio, tert-pentylthio, n-hexylthio, isohexylthio, 1-methylpenthylthio, and 2-methylpentylthio group, alkoxy groups possessing an ether bond such as methoxyethylene oxy group, alkylthio groups possessing an ether bond such as methoxyethylene thio group, alkoxy groups possessing a thioether bond such as methylthioethylene oxy group, alkylthio groups possessing a thioether bond such as methylthio-ethylene thio group, hydroxyalkoxy groups such as hydroxyethyl-eneoxy group, hydroxyalkylthio groups such as hydroxyethylenethio group, primary or secondary $C_1$–$C_6$ alkylamino groups such as methylamino, ethylamino, dimethylamino, and diethylamino group, primary or secondary $C_1$–$C_6$ hydroxyalkylamino groups such as hydroxyethylamino and di(hydroxyethyl)amino group, arylox groups optionally substituted with a hydroxyl group, a $C_1$–$C_4$ alkyl group, or a halogen atom such as phenoxy, p-hydroxyphenoxy, p-methylphenoxy, and p-chlorophenoxy group, arylthio groups optionally substituted with a hydroxyl group, a $C_1$–$C_4$ alkyl group, or a halogen atom such as phenylthio, p-hydroxyphenylthio, p-methylphenylthio, and p-chlorophenylthio group, arylamino groups optionally substituted with a hydroxyl group, a $C_1$–$C_4$ alkyl group, or a halogen atom such as anilino group, and aralkyloxy groups optionally substituted with a hydroxyl group, a $C_1$–$C_4$ alkyl group, or a halogen atom such as benzyloxy, p-methylbenzyloxy, and phenetyl oxy group may be cited besides the diphenyl compounds mentioned above. The term "$C_1$–$C_4$" alkyl group in the substituents mentioned above refers to methyl, ethyl, n-propyl, isopropyl, n-butyl, sec-butyl, and tert-butyl group and the term "halogen atoms" refers to chlorine, bromine, fluorine, and iodide.

The compounds represented by the general formula (I) can be produced in accordance with the reactions represented by the following formulas.

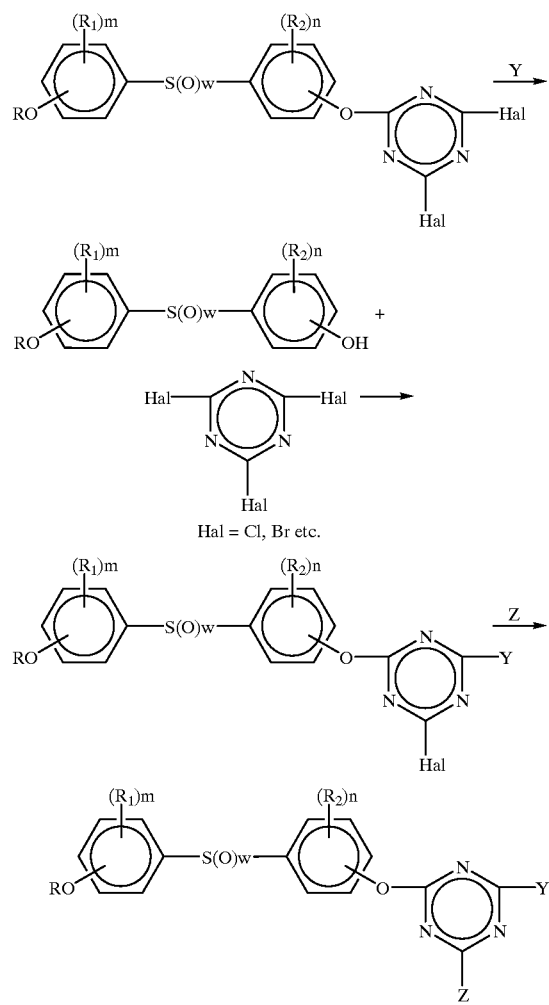

The method for the production of a triazine derivative represented by the formula (I) is preferred to be implemented in an organic solvent system in the presence of a basic substance. It is executed, for example, by causing the pertinent reactions to proceed in a water-soluble organic solvent such as, for example, acetonitrile, dimethyl sulfoxide or dimethyl formamide or in a water-insoluble organic solvent such as a benzene type organic solvent like benzene, toluene, chlorobenzene, or dichlorobenzene, a ketone type organic solvent like methyl isobutyl ketone or diethyl ketone, or an ester type organic solvent like ethyl acetate in the presence of an alkaline substance such as, for example, an inorganic substance represented by a carbonate or hydrogen carbonate of an alkali metal or alkaline earth metal, specifically sodium carbonate, potassium carbonate, calcium carbonate, sodium hydrogen carbonate, or potassium hydrogen carbonate or an organic substance represented by an amine, specifically triethyl amine, pyridine, or quinoline at a reaction temperature in the range of $-20°$ C.$\sim$$100°$ C. for a period in the range of several hours to ten-odd hours. By subsequently subjecting the resultant reaction mixture to selective extraction with a solvent, a simple compound having a high assay is obtained as the product aimed at.

This invention further contemplates those compounds which are represented by the general formula (II). These compounds are such triazine derivatives as possess S-containing diphenyl compounds represented by the general formula (I) and a triazine skeleton as component units thereof.

primary or secondary $C_1$–$C_6$ alkylamino group, a primary or secondary $C_1$–$C_6$ hydroxyalkylamino group, an aryloxy group optionally substituted with a hydroxyl group, a $C_1$–$C_4$ alkyl group, or a halogen atom, an arylthio group optionally substituted with a hydroxyl group, a $C_1$–$C_4$ alkyl group, or a halogen atom, an arylamino group optionally substituted with a hydroxyl group, a $C_1$–$C_4$ alkyl group, or a halogen atom, or an aralkyloxy group optionally substituted with a hydroxyl group, a $C_1$–$C_4$ alkyl group, or a halogen atom].

As concrete examples of the substituents, $R_1$–$R_8$, hydroxyl group, halogen atoms such as chlorine, bromine, fluorine, and iodine, $C_1$–$C_6$ alkyl groups such as methyl group, ethyl group, n-propyl group, isopropyl group, n-butyl group, sec-butyl group, tert-butyl group, n-pentyl group, iso-pentyl group, neopentyl group, tert-pentyl group, n-hexyl group, isohexyl group, 1-methylpentyl group, and 2-methylpentyl group, and $C_2$–$C_4$ alkenyl groups such as vinyl group, allyl group, isopropenyl group, 1-propenyl group, 2-butenyl group, 3-butenyl group, 1,3-butane dienyl group, and 2-methyl-2-propenyl group may be cited.

As concrete examples of Z, a hydrogen atom, a hydroxyl group, halogen atoms such as chlorine, bromine, fluorine, and iodine, $C_1$–$C_6$ alkoxy groups such as methoxy, ethoxy, n-propoxy, isopropoxy, n-butoxy, sec-butoxy, tert-butoxy, n-pentyloxy, isopentyloxy, neopentyloxy, tert-pentyloxyl, n-hexyloxy, isohexyloxy, 1-methylpentyloxy, and 2-methylpentyloxy group, $C_1$–$C_6$ alkylthio groups such as methylthio, ethylthio, n-propylthio, isopropylthio, n-butylthio, sec-butylthio, tert-butylthio, n-pentylthio,

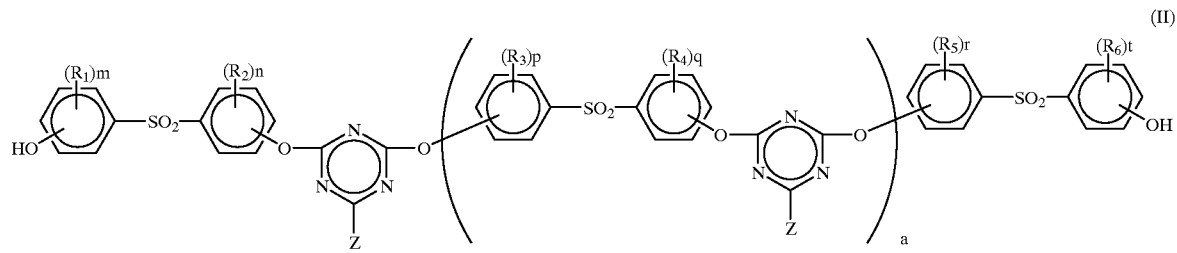

[wherein $R_1$–$R_6$, which may be the same or different, each represent a hydroxyl group, a halogen atom, a $C_1$–$C_6$ alkyl group, or a $C_2$–$C_4$ alkenyl group, m, n, p, q, r, and t each represent an integer of 0–4, providing that when the integer is not less than 2, $R_1$–$R_6$ may be different from one another, a represents an integer of 0–10, and Z represents a triazine derivative represented by the formula

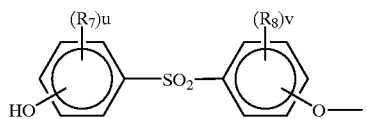

(wherein $R_7$ and $R_8$ which may be the same or different, each represent a hydroxyl group, a halogen atom, a $C_1$–$C_6$ alkyl group, or a $C_2$–$C_4$ alkenyl group, and u and v each represent an integer of 0–4, providing that where the integer is not less than 2, $R_7$ and $R_8$ may be different from each other) or a halogen atom, a hydroxyl group, a hydrogen atom, a $C_1$–$C_6$ alkoxy group, a $C_1$–$C_6$ alkylthio group, an alkoxy group possessing an ether bond, an alkylthio group possessing an ether bond, an alkoxy group possessing a thioether bond, an alkylthio group possessing a thioether bond, a hydroxyalkoxy group, a hydroxyalkylthio group, a isopentylthio, neopentylthio, tert-pentylthio, n-hexylthio, isohexylthio, 1-methylpentylthio, and 2-methylpentylthio group, alkoxy groups possessing an ether bond such as methoxyethyleneoxy group, alkylthio groups possessing an ether bond such methoxyethylene-thio group, alkoxy groups possessing a thioether bond such as methylthioethyleneoxy group, alkylthio groups possessing a thioether bond such as methylthioethylenethio group, hydroxyalkoxy groups such as hydroxyethyleneoxy group, hydroxyalkylthio groups such as hydroxyethylenethio group, primary or secondary $C_1$–$C_6$ alkylamino groups such as methylamino, ethylamino, dimethyl amino, and diethylamino group, primary or secondary $C_1$–$C_6$ hydroxyalkylamino groups such as hydroxyethylamino and di-(hydroxyethyl)amino group, aryloxy groups optionally substituted with a hydroxyl group, a $C_1$–$C_4$ alkyl group, or a halogen atom such as phenoxy, p-hydroxyphenoxy, p-methylphenoxy, and p-chlorophenoxy group, arylthio groups optionally substituted with a hydroxyl group, a $C_1$–$C_4$ alkyl group, or a halogen atom such as phenylthio, p-hydroxyphenylthio, p-methylphenylthio, and p-chlorophenylthio group, arylamino groups optionally substituted with a hydroxyl group, a $C_1$–$C_4$ alkyl group, or a halogen atom such as anilino group, and aralkyloxy groups optionally substituted with a hydroxyl group, a $C_1$–$C_4$ alkyl group, or a halogen atom such as benzyloxy, p-methylbenzyloxy, and phenetyloxy group may be cited besides the diphenyl sulfone compounds mentioned above. The term "$C_1$–$C_4$ alkyl group in the substituents mentioned above refers to methyl, ethyl, n-propyl, isopropyl, n-butyl, sec-butyl, and tert-butyl group and the term "halogen atoms" refers to chlorine, bromine, fluorine, and iodide.

The production of a triazine derivative represented by the general formula (II) is preferred to be carried out in an organic solvent or in a two-layer system of water and an organic solvent in the presence of a basic substance by a method represented by the following reaction formulas.

As the raw material, a 4,4'-dihydroxydiphenyl sulfone derivative or 2,4'-dihydroxydiphenyl sulfone derivative proves to be preferable by reason of ease of procurement.

in the presence of an alkaline substance such as, for example, a hydroxide of an alkali metal or alkaline earth metal, specifically sodium hydroxide, potassium hydroxide, or lithium hydroxide at a reaction temperature in the range $-20°$ C.~$150°$ C., preferably in the range of $30°$ C.–$120°$ C., for a period in the range of several hours to ten-odd hours.

By subsequently subjecting the resultant reaction mixture to selective extraction with a solvent and isolation by means of column chromatography, a simple compound having a high assay is obtained as the product aimed at.

This invention is further directed to a composition characterized by comprising not less than two species of triazine derivative represented by the general formula (II)

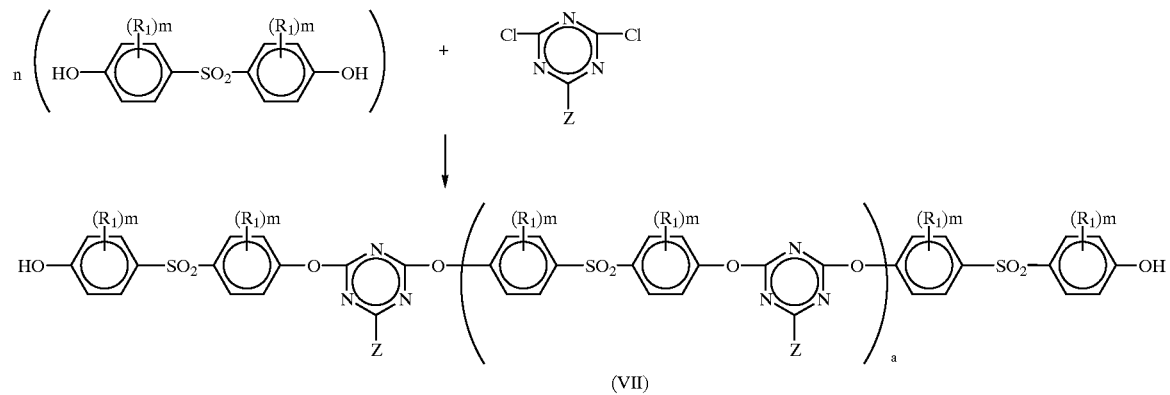

(VII)

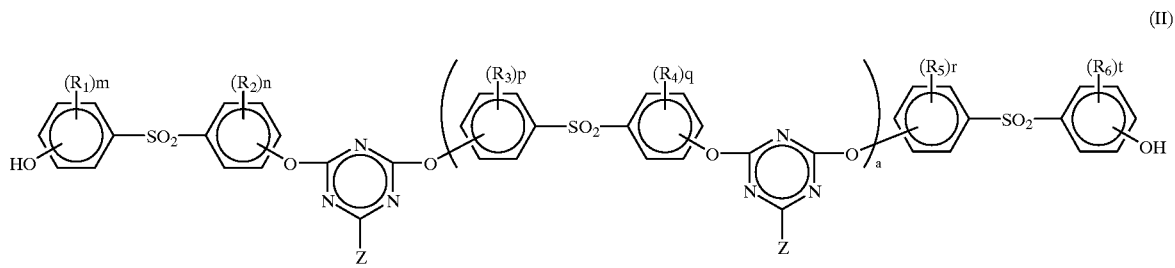

(II)

The reaction in an organic solvent is carried out in a water-soluble organic solvent such as acetonitrile, N,N-dimethyl formamide, or N,N-dimethyl acetamide in the presence of an organic amine such as triethyl amine, tributyl amine, pyridine, quinoline, or picoline at a reaction temperature in the range of 0~$120°$ C. for a period in the range of several hours—ten-odd hours.

The reaction in a two-layer system of water and an organic solvent is carried out in a water-insoluble organic solvent such as a benzene type organic solvent like benzene, toluene, chloro-benzene, or dichlorobenzene, a ketone type organic solvent like diethyl ketone or methylisobutyl ketone (MIBK), or an ester type organic solvent like ethyl acetate

[wherein $R_1$–$R_6$, m, n, p, q, r, t, a, and Z have the same meanings as mentioned above].

Though the contents of the two or more species of triazine derivative are arbitrary, the ratio of the compounds having a=0 and the compounds having a=1 or more in the general formula (II) is preferred to be such that the total proportion of the compounds having a=1 or more is in the range of 0.05–99 wt. %, specifically 1–90 wt. %, and more specifically 5–80 wt. %.

The composition is particularly preferable when it comprises not less than two species of the compound of the general formula (VII) which severally have different values of a and especially when one of the species of compound has a=0.

The composition of this invention can be produced by mixing, melting and mixing, or admixing in the course of synthetic crystallization the relevant compounds each in a powdery state or, where the two or more compounds severally have different values of a, by varying the conditions of production thereby allowing the plurality of compounds to be simultaneously formed and contained in a produced composition. This method of production enjoys simplicity of operation and permits the mixing ratio of the two or more compounds to be arbitrarily varied by varying the reaction ratios of the raw materials.

left reacting at 25° C. for 6 hours. After completion of the reaction, the reaction solution was caused to separate a water phase by addition of 100 ml of methyl isobutyl ketone (hereinafter abbreviated as "MIBK") and 200 ml of water. The organic solvent layer was washed with an aqueous 1% NaOH solution to recover the unaltered BPS and then the MIBK layer was concentrated and removed to afford 2.6 g of a colorless oil. When this oil was analyzed by high-speed liquid chromatography, it was found to contain 2,4-di[4-(4-

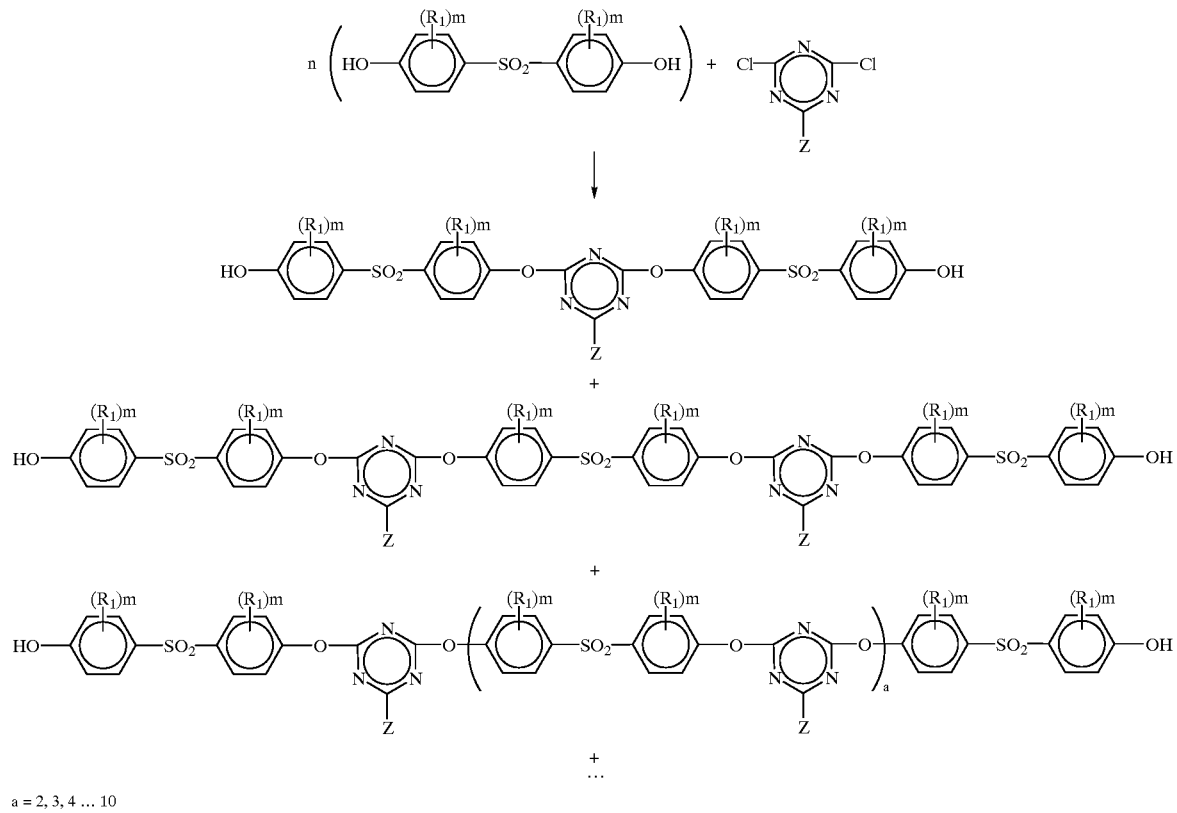

a = 2, 3, 4 ... 10

BEST MODE OF EMBODYING THE INVENTION

Now, the compounds of this invention will be specifically described below with reference to working examples. It should be noted, however, that this invention is not limited to these examples.

The compounds are identified by NMR and IR. The compounds and compositions of this invention have their crystal forms varied by the conditions prevailing during the separation of crystals such as, for example, the kind of solvent and the temperature of separation. There are times when they form an amorphous state or an adduct with a solvent. Their states of aggregate can be clarified by the melting point of crystals, infrared spectral analysis, thermal analysis, or X-ray analysis and they are embraced by the present invention.

EXAMPLE 1

In 100 ml of acetonitrile, 10.0 g (0.04 mol) of 4,4'-dihydroxydiphenyl sulfone (hereinafter abbreviated as "BPS") was placed, then 2.8 g (0.02 mol) of potassium carbonate was added, thereafter 1.8 g (0.01 mol) of 2,4-dichloro-6-methoxy-1,3,5-triazine was added, and they were hydroxyphenyl-sulfonyl)phenoxy-6-methoxy]-1,3,5-triazine, the compound aimed at, in a concentration of 44.4%. This oil was purified by column chromatography to obtain 1.0 g of white crystals of the compound having a melting point of 217–218° C. The compound was found by high-speed liquid chromatography to have an assay of 98.8%. The yield of this compound from 2,4-dichloro-6-methoxy-1,3,5-triazine, therefore, is 16%.

EXAMPLE 2

A reaction was performed at 25° C. for 4 hours by following the procedure of Example 1 while using 2.4 g (0.01 mol) of 2,4-dichloro-6-phenoxy-1,3,5-triazine in the place of the 2,4-dichloro-6-methoxy-1,3,5-triazine. After completion of the reaction, the reaction solution was caused to separate a water phase by addition of 100 ml of MIBK and 200 ml of water. The organic solvent layer was washed with an aqueous 1% NaOH solution to recover the unaltered BPS and the MIBK layer was concentrated and removed to obtain 2.7 g of a colorless oil. When the oil was analyzed by high-speed liquid chromatography, it was found to contain 2,4-di[4-(4-hydroxyphenylsulfonyl)phenoxy-6-phenoxy]-3,5-triazine, the compound aimed at, in a concentration of 44.8%. This oil was purified by column chromatography to obtain 1.6 g of white crystals of the compound having a melting point of 230–232° C. The compound was found by high-speed liquid chromatography to have an assay of 95.4%. The yield of this compound from 2,4-dichloro-6-phenoxy-1,3,5-triazine, therefore, is 24%.

EXAMPLE 3

A reaction was performed at 40° C. for 7 hours by following the procedure of Example 1 while using 2.4 g (0.01 mol) of 2-anilino-4,6-dichloro-1,3,5-triazine in the place of the 2,4-dichloro-6-methoxy-1,3,5-triazine. After completion of the reaction, the reaction solution was caused to separate a water phase by addition of 100 ml of MIBK and 200 ml of water. The organic solvent layer was washed with an aqueous 1% NaOH solution to recover the unaltered BPS and subsequently the MIBK layer was concentrated and removed to obtain 4.6 g of a colorless oil. When the oil was analyzed by high-speed liquid chromatography, it was found to contain 2-anilino-4,6-di[4-(4-hydroxyphenyl-sulfonyl) phenoxy]-1,3,5-triazine, the compound aimed at, in a concentration of 62.5%. This oil was purified by column chromatography to obtain 1.8 g of white crystals of the compound having a melting point of 211–214° C. The compound was found by high-speed liquid chromatography to have an assay of 96.3%. The yield of this compound from 2-anilino-4,6-dichloro-1,3,5-triazine, therefore, is 27%.

EXAMPLE 4

In 100 ml of acetonitrile, 5.6 g (0.044 mol) of 4-mercaptophenol was placed, then 4.2 g (0.04 mol) of sodium carbonate was added, thereafter 7.4 g (0.04 mol) of CC was added, and they were left reacting at 0–5° C. for one hour. The reaction solution and 40.0 g (0.16 mol) of BPS, 100 ml of acetonitrile, and 11.0 g (0.08 mol) of potassium carbonate added sequentially thereto in the order mentioned were left reacting at 40° C. for five hours. After completion of the reaction, the reaction solution was caused to separate a water phase by addition of 200 ml of MIBK and 200 ml of water. The organic solvent layer was washed with an aqueous 1% NaOH solution to recover the unaltered BPS and then the MIBK layer was concentrated and removed to afford 6.2 g of a light yellow oil. When this oil was analyzed by high-speed liquid chromatography, it was found to contain 2,4-di[4-(4-hydroxyphenylsulfonyl)phenoxy]-6-(4-hydroxyphenyl)thio-1,3,5-triazine, the compound aimed at, in a concentration of 79.7%. This oil was purified by column chromatography to obtain 2.3 g of white crystals of the compound having a melting point of 123–125° C. The compound was found by high-speed liquid chromatography to have an assay of 98.8%. The yield of this compound from CC, therefore, is 16%.

Typical examples of the triazine derivatives of the present invention represented by the general formula (I) including those of the working examples are shown in Table 1.

TABLE 1

Structure: triazine with substituents E, Y, Z:

$$\text{E-}\underset{\underset{N}{\|}}{\overset{\overset{N}{\|}}{C}}\text{-Y, Z on triazine ring}$$

| Compound No. | E | Y | Z | Melting point (°C) |
|---|---|---|---|---|
| 1 | HO–C₆H₄–SO₂–C₆H₄–O– | HO–C₆H₄–SO₂–C₆H₄–O– | CH₃O– | 217–218 |
| 2 | " | " | C₂H₅O– | 147–150 |
| 3 | " | " | n-C₃H₇O– | |
| 4 | " | " | i-C₃H₇O– | 175–178 |
| 5 | " | " | C₄H₉O– | 136–140 |
| 6 | " | " | C₅H₁₁O– | |
| 7 | " | " | C₆H₁₃O– | 132–135 |
| 8 | " | " | C₆H₅–O– (phenoxy with OCH₃) | 230–232 |
| 9 | " | " | CH₃O(CH₂)₂O– | |
| 10 | " | " | cyclohexyl–O– | 174–176 |
| 11 | " | " | HO(CH₂)₂O– | |
| 12 | " | " | HO–C₆H₄–O– (with OCH₃) | |
| 13 | " | " | HO–C₆H₄–O– (meta, with OCH₃) | |

TABLE 1-continued

| No. | Ar | R | mp (°C) |
|---|---|---|---|
| 14 | 2-methoxyphenol (guaiacyl) | | |
| 15 | " | CH$_3$S— | |
| 16 | " | C$_2$H$_5$S— | |
| 17 | " | C$_6$H$_5$S— | |
| 18 | " | HO(CH$_2$)$_2$S— | 123–125 |
| 19 | " | 4-HO-C$_6$H$_4$-S— | |
| 20 | " | H$_2$N— | 158–162 |
| 21 | " | CH$_3$NH— | 159–161 |
| 22 | " | C$_2$H$_5$NH— | |
| 23 | " | n-C$_3$H$_7$NH— | 211–214 |
| 24 | " | C$_6$H$_5$NH— | |
| 25 | " | (CH$_3$)$_2$N— | 150–155 |
| 26 | " | (C$_2$H$_5$)$_2$N— | |
| 27 | " | (n-C$_4$H$_9$)$_2$N— | 219–221 |
| 28 | 4-HO-C$_6$H$_4$-SO$_2$-C$_6$H$_4$- (4-methoxy) | HO(CH$_2$)$_2$NH— | 149–153 |
| 29 | " | HO(CH$_2$)$_3$NH— | 233–240 |
| 30 | " | HO— | 152–156 |
| 31 | " | Cl— | 179–183 |
| 32 | 4-HO-C$_6$H$_4$-SO$_2$-C$_6$H$_4$-OCH$_3$ | HO— | 160–162 |
| 33 | " | Cl— | |
| 34 | " | CH$_3$O— | |

TABLE 1-continued

| No. | Structure A | Structure B | R |
|---|---|---|---|
| 35 | 4-(4-methoxyphenylsulfonyl)-2-hydroxyphenyl | 4-(4-methoxyphenylsulfonyl)-2-hydroxyphenyl | $CH_3O—$ |
| 36 | '' | '' | $C_2H_5O—$ |
| 37 | '' | '' | $n\text{-}C_3H_7O—$ |
| 38 | '' | '' | $i\text{-}C_3H_7O—$ |
| 39 | '' | '' | $C_4H_9O—$ |
| 40 | '' | '' | $C_5H_{11}O—$ |
| 41 | '' | '' | $C_6H_{13}O—$ |
| 42 | '' | '' | phenoxy ($C_6H_5O—$) |
| 43 | '' | '' | 4-hydroxyphenoxy |
| 44 | '' | '' | 4-hydroxyphenylthio |
| 45 | '' | '' | N-methyl-phenylamino |
| 46 | '' | '' | $HO—$ |
| 47 | '' | '' | $Cl—$ |
| 48 | '' | '' | $HO—$ |
| 49 | '' | '' | $CH_3O—$ |
| 50 | '' | '' | $CH_3O—$ |
| 51 | 4-(2-methoxyphenylsulfonyl)-4-hydroxyphenyl | 4-(2-methoxyphenylsulfonyl)-4-hydroxyphenyl | $CH_3O—$ |
| 52 | '' | '' | $C_2H_5O—$ |
| 53 | '' | '' | $n\text{-}C_3H_7O—$ |

TABLE 1-continued

| | | |
|---|---|---|
| 54 | " | i-C$_3$H$_7$O— |
| 55 | " | C$_4$H$_9$O— |
| 56 | " | C$_5$H$_{11}$O— |
| 57 | " | C$_6$H$_{13}$O— |
| 58 | " | 4-methoxyphenyl (—C$_6$H$_4$—O—CH$_3$) |
| 59 | " | 4-hydroxyphenoxy (HO—C$_6$H$_4$—O—) |
| 60 | " | 4-hydroxyphenylthio (HO—C$_6$H$_4$—S—) |
| 61 | " | phenylamino (C$_6$H$_5$—NH—) |
| 62 | " | HO— |
| 63 | " | Cl— |
| 64 | " | HO— |
| 65 | " | Cl— |
| 66 | " | CH$_3$O— |
| 67 | 2-methoxyphenyl-SO$_2$-(4-hydroxyphenyl) | CH$_3$O— |
| 68 | 4-methoxyphenyl-SO$_2$-(2-hydroxyphenyl) | C$_2$H$_5$O— |
| 69 | " | n-C$_3$H$_7$O— |
| 70 | " | i-C$_3$H$_7$O— |
| 71 | " | C$_4$H$_9$O— |
| 72 | " | C$_5$H$_{11}$O— |
| 73 | " | C$_6$H$_{13}$O— |
| 74 | " | 4-methoxyphenyl (—C$_6$H$_4$—O—CH$_3$) |

TABLE 1-continued
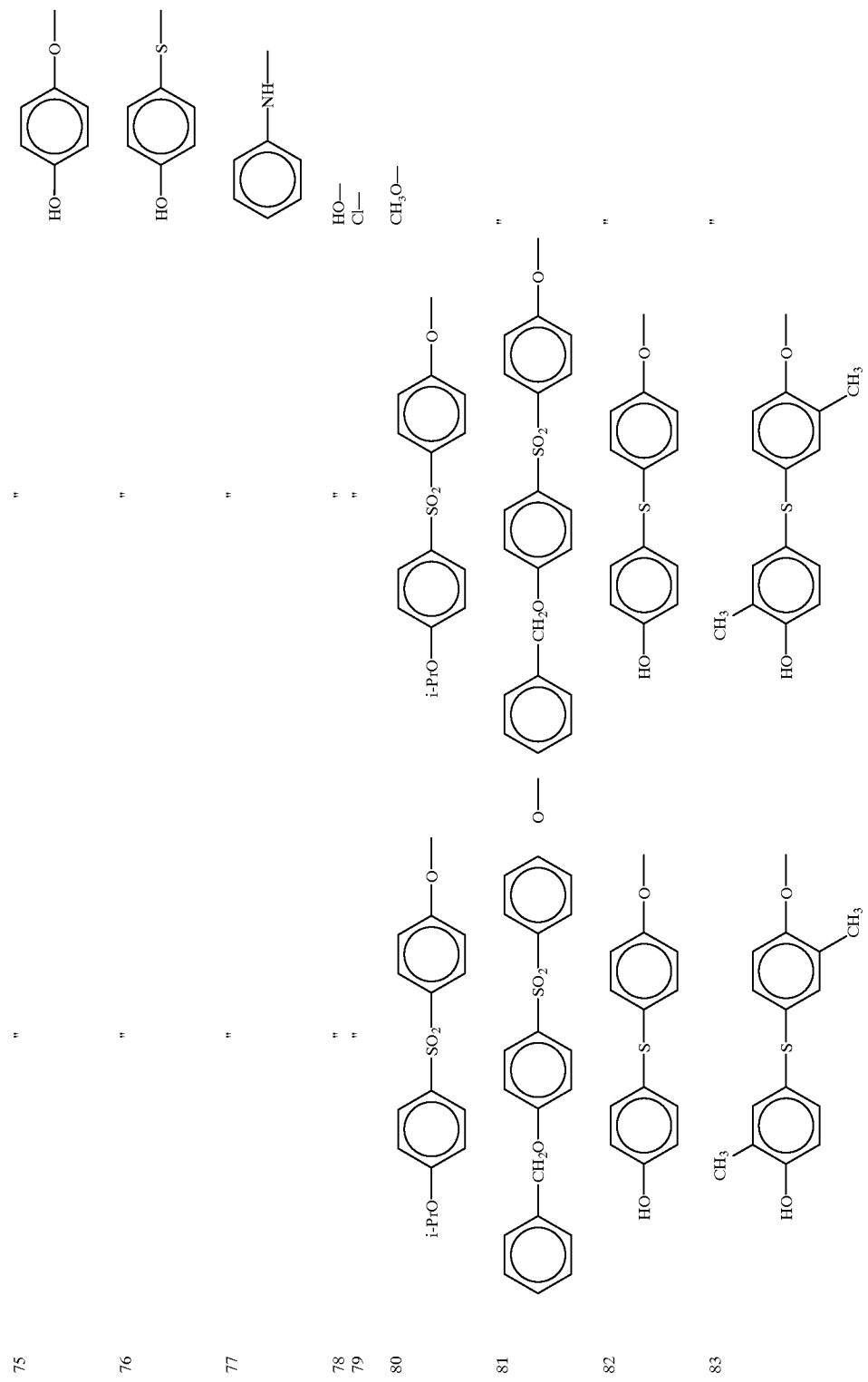

TABLE 1-continued

| | | | |
|---|---|---|---|
| 84 | (structure) | (structure) | " |
| 85 | (structure) | (structure) | —Cl |
| 86 | | | —OH |
| 87 | | | —OH |
| 88 | | | —Cl |
| 89 | (structure) | (structure) | —Cl |
| 90 | | | —OH |
| 91 | | | —OH |
| 92 | | | —Cl |
| 93 | (structure) | (structure) | —Cl |
| 94 | | | —OH |
| 95 | | | —OH |
| 96 | | | —Cl |
| 97 | (structure) | (structure) | —Cl |
| 98 | | | —OH |
| 99 | | | —OH |
| 100 | | | —Cl |

TABLE 1-continued
| Compound No. | | | | Melting point (° C.) |
|---|---|---|---|---|
| 101 |  |  | —Cl | |
| 102 | " | " | —OH | |
| 103 | " | " | —OH | |
| 104 | " | " | —Cl | |
E 
| Compound No. | E | | | Melting point (° C.) |
|---|---|---|---|---|
| 105 |  | | | 250° C. or more decomposed |
| 106 |  | | | |
| 107 |  | | | |
| 108 |  | | | |

TABLE 1-continued
| | |
|---|---|
| 109 | 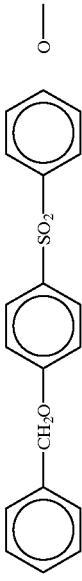 |
| 110 |  |
| 111 | 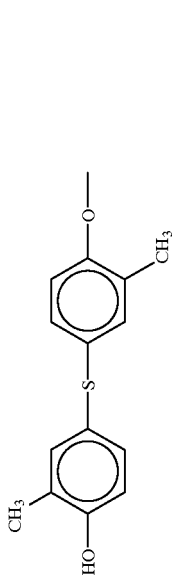 |
| 112 | 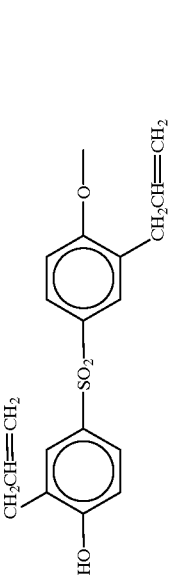 |
| E = | 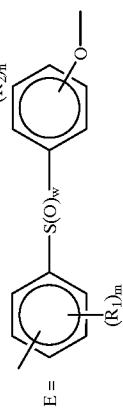 |

EXAMPLE 5

Synthesis of 4,4'-bis[2-(4-hydroxyphenylsulfonyl)-phenoxy-4-methoxy-1,3,5-triazin-6-yloxy]diphenyl sulfone In 200 ml of acetonitrile, 30.0 g (0.12 mol) of 4,4-dihydroxydiphenyl sulfone (hereinafter abbreviated as "BPS") was placed, then 5.4 g (0.03 mol) of 2,4-dichloro-6-methoxy-1,3,5-triazine was added, a solution of 6.1 g (0.06 mol) of triethyl amine in 50 ml of acetonitrile was slowly added dropwise, and they were left reacting at 25° C. for two hours. After completion of the reaction, the reaction solution was caused to separate a water phase by addition of 300 ml of methylisobutyl ketone (hereinafter abbreviated as "MIBK") and 200 ml of water. The organic solvent layer was washed with an aqueous 1% NaOH solution to recover the unaltered BPS and then the MIBK layer was concentrated and removed to afford 14.7 g of a light yellow oil. This oil was purified by column chromatography to obtain 1.3 g of white crystals of the compound (having a melting point of 180–182° C.). It was found by high-speed liquid chromatography to have an assay of 97.9%. The yield of this compound from 2,4-dichloro-6-methoxy-1,3,5-triazine, therefore, is 5%.

The following compounds may be cited as typical examples of the compounds of this invention represented by the general formula (II) including those of the present working example.

(2-1) 4,4'-Bis[2-(4-hydroxyphenylsulfonyl)phenoxy-4-methoxy-1,3,5-triazin-6-yloxy]diphenyl sulfone, m.p. 180–182° C.
(2-2) 4,4'-Bis[4-(4-hydroxyphenylsulfonyl)phenoxy-2-diethylamino-1,3,5-triazin-6-yloxy]diphenyl sulfone, m.p. 169–175° C.
(2-3) 4,4'-Bis[4-(4-hydroxyphenylsulfonyl)phenoxy-2-hydroxy-1,3,5-triazin-6-yloxy]diphenyl sulfone
(2-4) 4,4'-Bis[4-(4-hydroxyphenylsulfonyl)phenoxy-2-ethoxy-1,3,5-triazin-6-yloxy]diphenyl sulfone
(2-5) 4,4'-Bis[2-(4-hydroxyphenylsulfonyl)phenoxy-4-isopropoxy-1,3,5-triazin-6-yloxy]diphenyl sulfone
(2-6) 4,4'-Bis[2-(4-hydroxyphenylsulfonyl)phenoxy-4-propoxy-1,3,5-triazin-6-yloxy]diphenyl sulfone
(2-7) 4,4'-Bis[4-(4-hydroxyphenylsulfonyl)phenoxy-2-butoxy-1,3,5-triazin-6-yloxy]diphenyl sulfone
(2-8) 4,4'-Bis[4-(4-hydroxyphenylsulfonyl)phenoxy-2-hexyloxy-1,3,5-triazin-6-yloxy]diphenyl sulfone
(2-9) 4,4'-Bis[(2-(4-hydroxyphenylsulfonyl)phenoxy-4-phenoxy-1,3,5-triazin-6-yloxy]diphenyl sulfone
(2-10) 4,4'-Bis[(4-(4-hydroxyphenylsulfonyl)phenoxy-2-anilino-1,3,5-triazin-6-yloxy]diphenyl sulfone
(2-11) 4,4'-Bis[2-(4-hydroxyphenylsulfonyl)phenoxy-4-(4-hydroxyphenyl)thio-1,3,5-triazin-6-yloxy]diphenyl sulfone
(2-12) 4,4'-Bis[2-(4-hydroxyphenylsulfonyl)phenoxy-4-methylamino-1,3,5-triazin-6-yloxy]diphenyl sulfone, m.p. 198–204° C.
(2-13) 4,4'-Bis[4-(4-hydroxyphenylsulfonyl)phenoxy-2-ethylamino-1,3,5-triazin-6-yloxy]diphenyl sulfone
(2-14) 4,4'-Bis[2-(4-hydroxyphenylsulfonyl)phenoxy-4-propylamino-1,3,5-triazin-6-yloxy]diphenyl sulfone, m.p. 201–207° C.
(2-15) 4,4'-Bis[4-(4-hydroxyphenylsulfonyl)phenoxy-2-butylamino-1,3,5-triazin-6-yloxy]diphenyl sulfone
(2-16) 4,4'-Bis[4-(4-hydroxyphenylsulfonyl)phenoxy-2-dimethylamino-1,3,5-triazin-6-yloxy]diphenyl sulfone, m.p. 179–184° C.
(2-17) 4,4'-Bis[4-(4-hydroxyphenylsulfonyl)phenoxy-2-dibutylamino-1,3,5-triazin-6-yloxy]diphenyl sulfone
(2-18) 2,4'-Bis[2-(2-hydroxyphenylsulfonyl)phenoxy-4-methoxy-1,3,5-triazin-6-yloxy]diphenyl sulfone
(2-19) 2,4'-Bis[2-(4-hydroxyphenylsulfonyl)phenoxy-4-methoxy-1,3,5-triazin-6-yloxy]diphenyl sulfone
(2-20) 4,4'-Bis[3,5-dimethyl-2-(3,5-dimethyl-4-hydroxyphenylsulfonyl)phenoxy-4-methoxy-1,3,5-triazin-6-yloxy]diphenyl sulfone
(2-21) 4,4-Bis[3-allyl-4-hydroxyphenyl-sulfonyl)phenoxy-4-methoxy-1,3,5-triazin-6-yloxy]diphenyl sulfone

EXAMPLE 6

In 300 ml of water, 4.8 g (0.2 mol) of sodium hydroxide was dissolved, 30.0 g (0.12 mol) of BPS was added, then 7.2 g (0.04 mol) of 2,4-dichloro-6-methoxy-1,3,5-triazine was slowly added, and thereafter they were left reacting at 30° C. for 12 hours. After the reaction, the reaction solution and 1.0 g (25 m.mols) of sodium hydroxide added thereto were filtered together to remove the unaltered BPS. The resultant crude crystals were dissolved in 600 ml of ethyl acetate, washed with water, and concentrated. The concentrated solution was recrystallized from 100 ml of toluene and 100 ml of ethyl acetate to obtain 18.0 g of white crystals. By high-speed liquid chromatography, these crystals were found to contain 6-methoxy-2,4-di[4-(4-hydroxyphenylsulfonyl)phenoxy]-1,3,5-triazine in a concentration of 92.0% and 4,4'-bis[2-(4-hydroxyphenylsulfonyl)phenoxy-4-methoxy-1,3,5-triazin-6-yloxy]diphenyl sulfone in a concentration of 3.5%. The yield of the compound from 2,4-dichloro-6-methoxy-1,3,5-triazine, therefore, is 74%.

EXAMPLE 7

In 200 ml of acetonitrile, 75.0 g (0.3 mol) of BPS and 19.3 g (0.1 mol) of 6-dimethylamino-2,4-dichloro-1,3,5-triazine were dissolved and 30.3 g (0.3 mol) of triethylamine added thereto at 25° C. were together left reacting at 75–80° C. for 8 hours. After completion of the reaction, the reaction solution was poured in 300 ml of MIBK and 300 ml of water. The MIBK layer separated consequently was washed several times with an aqueous 0.5% NaOH solution to remove BPS. The MIBK layer was concentrated to obtain 46.5 g of the following composition having a boiling point of 121–127° C.

The yield of the compound from 2,4-dichloro-6-dimethylamino-1,3,5-triazine, therefore, is 75%.

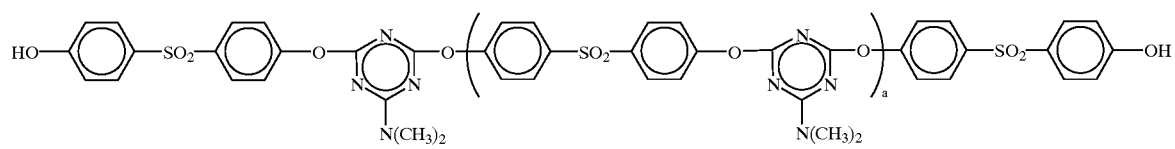

The compound, by high-speed liquid chromatography using a column (made by Kanto Kagaku K.K. and sold under the trademark designation of "Mightysil RP-18"), a mobile phase of CH$_3$CN:H$_2$O:1% H$_3$PO$_4$=750:250:5, and a UV wavelength of 260 nm, was found to have the following composition.

a=0: Retention time 2.0 minutes, area % 47.8%
a=1: Retention time 2.5 minutes, area % 21.0%
a=2: Retention time 3.3 minutes, area % 12.4%
a=3: Retention time 4.6 minutes, area % 7.4%
a=4: Retention time 6.7 minutes, area % 4.5%
a=5: Retention time 9.0 minutes, area % 2.3%
a=6: Retention time 14.8 minutes, area % 1.5%

EXAMPLE 8

In 200 ml of acetonitrile, 37.5 g (0.15 mol) of BPS and 19.3 g (0.1 mol) of 2,4-dichloro-6-dimethylamino-1,3,5-triazine were dissolved and 25.3 g (0.25 mol) of triethylamine was added at 25° C. and they were together left

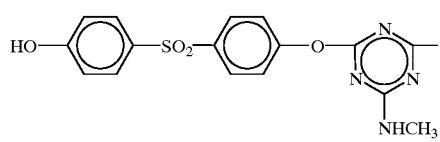

reacting at 75–80° C. for 8 hours. After completion of the reaction, the reaction solution was pored in 300 ml of MIBK and 300 ml of water. The MIBK layer consequently separated was washed several times with an aqueous 0.5% NaOH solution to remove the BPS. The MIBK layer was concentrated to obtain 40.3 g of the following composition having a melting point of 123–132° C.

The yield of this composition from 2,4-dichloro-6-dimethyl-amino-1,3,5-triazine, therefore, is 65%.

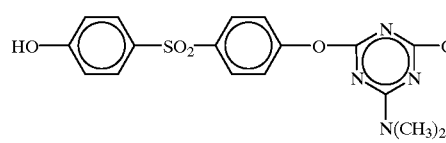

The compound, by high-speed liquid chromatography using a column (made by Kanto Kagaku K.K. and sold under the trademark designation of "Mightysil RP-18"), a mobile phase of CH$_3$CN:H$_2$O:1% H$_3$PO$_4$=750:250:5, and a UV wavelength of 260 nm, was found to have the following composition.

a=0: Retention time 2.0 minutes, area % 22.6%
a=1: Retention time 2.5 minutes, area % 23.1%
a=2: Retention time 3.3 minutes, area % 17.4%
a=3: Retention time 4.6 minutes, area % 12.8%
a=4: Retention time 6.7 minutes, area % 8.6%
a=5: Retention time 9.9 minutes, area % 5.6%
a=6: Retention time 14.8 minutes, area % 3.8%

EXAMPLE 9

By following the procedure of Example 7 while substituting 17.9 g (0.1 mol) of 2,4-dichloro-6-methylamino-1,3,5-triazine for the 2,4-dichloro-6-dimethylamino-1,3,5-triazine, 42.4 g of the following composition was obtained. This composition had a melting point of 195–205° C.

The yield of this composition from 2,4-dichloro-6-methyl-amino- 1,3,5-triazine, therefore, is 70%.

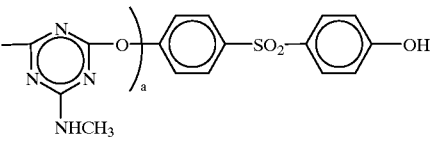

The compound, by high-speed liquid chromatography using a column (made by Kanto Kagaku K.K. and sold under the trademark designation of "Mightysil RP-18"), a mobile phase of H$_2$O:1% H$_3$PO$_4$=750:250:5, and a UV wavelength of 260 nm, was found to have the following composition.

a=0: Retention time 2.5 minutes, area % 44.4%
a=1: Retention time 2.9 minutes, area % 19.6%
a=2: Retention time 3.4 minutes, area % 13.0%
a=3: Retention time 4.0 minutes, area % 8.9%
a=4: Retention time 4.9 minutes, area % 5.6%
a=5: Retention time 5.9 minutes, area % 2.4%
a=6: Retention time 7.1 minutes, area % 1.0%

EXAMPLE 10

By following the procedure of Example 8 while substituting 17.9 g (0.1 mol) of 2,4-dichloro-6-methylamino-1,3,5-triazine for the 2,4-dichloro-6-dimethylamino-1,3,5-triazine, 32.1 g of the following composition was obtained. This composition had a melting point of 195–205° C.

The yield of this composition from 2,4-dichloro-6-methyl-amino-1,3,5-triazine, therefore, is 53%.

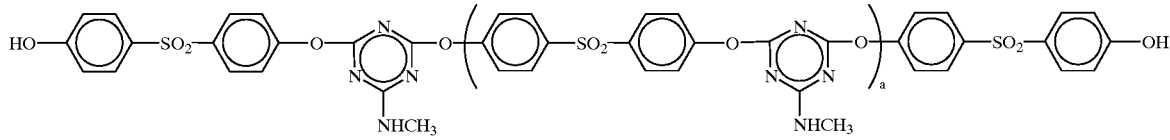

The compound, by high-speed liquid chromatography using a column (made by Kanto Kagaku K.K. and sold utider the trademark designation of "Mightysil RP-18"), a mobile phase of $CH_3CN:H_2O:1\% \ H_3PO_4=750:250:5$, and a UV wavelength of 260 nm, was found to have the following composition.

a=0: Retention time 2.5 minutes, area % 24.9%
a=1: Retention time 2.9 minutes, area % 32.1%
a=2: Retention time 3.4 minutes, area % 19.0%
a=3: Retention time 4.0 minutes, area % 11.1%
a=4: Retention time 4.9 minutes, area % 6.0%
a=5: Retention time 5.9 minutes, area % 2.9%
a=6: Retention time 7.1 minutes, area % 1.5%

Examples of the combination of compositions containing not less than two species of compound represented by the general formula (II) are cited below.

(3-1) Combination of 4-methoxy-2,4-di[4-(4-hydroxyphenyl-sulfonyl)phenoxy]-1,3,5-triazine and 4,4'-bis[2-(4-hydroxyphenyl-sulfonyl)phenoxy-4-methoxy-1,3,5-triazin-6-yloxy]diphenyl sulfone (3-2) Combination of 4-phenoxy-2,4-di[4-(4-hydroxyphenyl-sulfonyl)phenoxy]-1,3,5-triazine and 4,4'-bis[2-(4-hydroxyphenyl-sulfonyl)phenoxy-4-phenoxy-1,3,5-triazin-6-yloxy]diphenyl sulfone (3-3) Combination of 2-anilino-4,6-di[4-(4-hydroxyphenyl-sulfonyl)phenoxy]-1,3,5-triazine and 4,4'-bis[4-hydroxyphenyl-sulfonyl)phenoxy-2-anilino-1,3,5-triazin-6-yloxy]diphenyl sulfone (3-4) Combination of 6-(4-hydroxyphenyl)thio-2,4-di[4-(4-hydroxyphenylsulfonyl)phenoxy]-1,3,5-triazine and 4,4'-bis[2-(4-hydroxyphenylsulfonyl)phenoxy-4-(4-hydroxyphenyl)thio-1,3,5-triazin-6-yloxy]diphenyl sulfone (3-5) Combination of 2-diethylamino-4,6-di[4-(4-hydroxyphenylsulfonyl)phenoxy]-1,3,5-triazine and 4,4'-bis[4-(4-hydroxyphenylsulfonyl)phenoxy-2-diethylamino-1,3,5-triazin-6-yloxy]diphenyl sulfone (3-6) Combination of 6-methoxy-1,4-di[4-(4-hydroxyphenyl-sulfonyl)phenoxy]-1,3,5-triazine, 4,4'-bis[2-(4-hydroxyphenyl-sulfonyl)phenoxy-4-methoxy-1,3,5-triazin-6-yloxy]diphenyl sulfone, and 6-methoxy-2,4-di[4-[2-(4-hydroxyphenylsulfonyl)-phenoxy-4-methoxy-1,3,5-triazin-6-yloxy]phenylsulfonyl]phenoxy-1,3,5-triazine This invention is further directed to a recording material containing a coloring dye, which is characterized by containing at least one species of a triazine derivative represented by the general formula (I) or general formula (II).

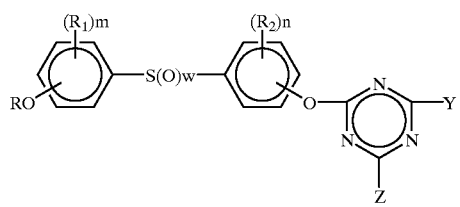

(I)

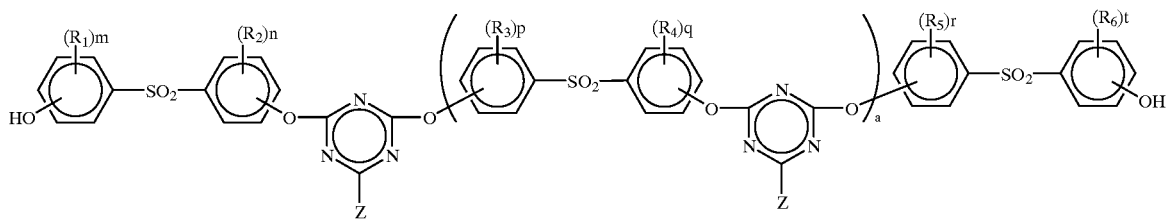

(II)

(wherein $R_1$–$R_6$, m, n, p, q, r, t, a, R, Y, and Z have the same meanings as mentioned above).

The compounds of this invention can be used in a recording material containing a coloring dye irrespectively of the type of application. They can be utilized as thermal printing materials or pressure-sensitive copying materials, for example.

What deserves special notice about the compounds of this invention is the fact that these compounds can be used as developers excelling in resistance to plasticizers or as stabilizers of image conservation possessed of resistance to plasticizers.

The recording material containing a coloring dye can be produced by any of the methods which are in popular use. The recording material which is intended for the stabilizer of image conservation is produced by using the compounds in conjunction with an additional developer and auxiliaries such as sensitizer and the recording material which is intended for the developer is produced by using the compounds in conjunction with such auxiliaries as sensitizer. It is naturally permissible to combine compounds of this invention in two sets, the one set to be used for the stabilizer of image conservation and the other set for the developer. It is also permissible to produce a recording material endowed with a characteristic coloring property by combining compounds of this invention with compounds intended for the same purpose.

The fact that the compounds of this invention possess the characteristics which fit the two uses, i.e. the stabilizer of image conservation and the developer, proves to be extremely advantageous in respect that the compounds permit manufacture of a recording material to be inexpensively fulfilled by decreasing the amounts of the stabilizer of image conservation and the developer to be used relative to the amount of the coloring dye.

The compound of this invention is used in a thermal printing material in the same manner as when it is used in known stabilizer of image conservation and developer. The thermal printing material can be manufactured, for example, by dispersing minute particles of the compound of this invention and minute particles of a coloring dye severally in separate portions of an aqueous solution of such a water-soluble binder as polyvinyl alcohol or cellulose, mixing the resultant suspensions, applying the produced mixture to a substrate like paper, and drying the wet substrate.

The ratio of the amount of the compound of this invention to the amount of the coloring dye is in the range of 0.1–5 parts by weight, preferably 0.2–2 parts by weight, based on one part by weight of the coloring dye where a stabilizer of image conservation is aimed at or in the range of 1–10 parts by weight, preferably 1.5–5 parts by weight, based on one part by weight of the coloring dye where a developer is aimed at.

In the compounds of this invention which are represented by the general formula (II), it is effective herein to use a compound having a=0 in combination with at least one species of compound having a=1 or more. In this case, while the compound having a=0 and the compound having a=1 or more may be used in such a relation as generally exists between a developer and a stabilizer of image, they are characterized by having their effects exalted conspicuously even when they are used in such proportions that the compound having a=0 incorporates therein the compound having a=1 or more.

The gravimetric ratio of the content of the compound having a=0 to the content of the compound having a=1 or more is in the range of 100:0.05–1:99, preferably 99:1–10:90, and particularly preferably 95:5–20:80. This ratio is preferred to be in the range of 50:50–20:80 where the ability to conserve is required to be particularly high or in the range of 95:5–50:50 where the sensitivity is also required to be high.

When a plurality of compounds having a =1 or more are involved, the numerical values of gravimetric ratios mentioned above are totals of weights of the relevant compounds.

As respects the method of mixing to be involved where two or more species of compound of the general formula (II) are used, the plurality of compounds may be mixed in the form of powder, they may be added during the preparation and dispersion of a coating liquid, or they may be added in the form of a dispersion. By selecting methods for producing the relevant compounds, a composition which contain the plurality of compounds altogether may be used. This composition proves to be very effective when it is used as a developer.

The compounds and compositions of the present invention embrace compounds which are similar in constitution but dissimilar in degree of crystallization or crystal form, compounds which are in an amorphous state, and compounds which are adducts of a solvent as mentioned above. The use of these compounds possibly results in improving the produced recording materials in texture of background and sensitivity. The decrease in particle diameter of these compounds in a coating liquid possibly results in enhancing the sensitivity. Particularly, the compounds which have a high degree of crystallization excel those which are in an amorphous state in terms of whiteness and heat resistance of the background. The dispersion mentioned above is allowed to incorporate therein an additional developer, an additional image stabilizer, sensitizer, filler, dispersing agent, antioxidant, desensitizer, viscosity inhibitor, defoaming agent, light stabilizer, and fluorescent whitening agent as occasion demands.

These additive chemicals may be incorporated in a coloring layer. Where the recording material happens to have a multilayer structure, they may be contained in any of the component layers such as, for example, a protective layer. Particularly when an overcoat layer or an undercoat layer is provided on or below the coloring layer, these layers are allowed to incorporate therein an antioxidant and a light stabilizer. The antioxidant and light stabilizer, when necessary, may be incorporated in the layers as enclosed in microcapsules.

As concrete examples of the coloring dye to be used in the recording material of this invention, Fluoran type, phthalide type, lactam type, triphenylmethane type, phenothiazine type, and spiropyrane type leuco dyes may be cited. The coloring dye imposes no restriction particularly but requires only to be capable of generating color on contact with a developer which is an acidic substance. Naturally, this coloring dye is used alone to manufacture a recording material of the color which is generated by the coloring dye. It is permissible to use two or more such coloring dyes in a mixed state. A recording material which generates a genuine black color, for example, may be produced by using coloring dyes of three primary colors, red, blue, and green, optionally as mixed with a black coloring dye.

As concrete examples of the fluorane type dye, 3-diethylamino-6-methyl-7-anilinofluorane, 3-dibutylamino-6-methyl-7-anilinofluorane, 3-(N-ethyl-N-isobutylamino)-6-methyl-7-anilino-fluorane, 3-(N-methyl-N-propylamino)-6-methyl-7-anilinofluorane, 3-(N-ethyl-N-isopentylamino)-6-methyl-7-anilinofluorane, 3-diethylamino-7-(o-chloroanilino)fluorane, 3-dibutylamino-7-(o-chloroanilino) fluorane, 3-(N-ethyl-p-toluidino)-6-methyl-7-anilinofluorane, 3-(N-cyclohexyl-N-methylamino)-6-methyl-7-anilinofluorane, 3-pyrrolidino-6-methyl-7-anilinofluorane, 3-piperidino- 6-methyl-7-anilinofluorane, 3-dimethylamino-7-(m-trifluoromethylanilino)fluorane, 3-dipentylamino-6-methyl-7-anilinofluorane, 3-(N-ethoxypropyl-N-ethylamino)-6-methyl-7-anilinofluorane, 3-dibutylamino-7-(o-fluoroanilino)fluorane, 3-diethylaminobenz[a]fluorane, 3-dimethylamino-6-methyl-7-chloro-fluorane, 3-diethylamino-5-methyl-7-dibenzylaminofluorane, 3-diethylamino-7-dibenzylaminofluorane, 3-diethylamino-5-chloro-fluorane, 3-diethylamino-6-(N,N'-dibenzylamino)fluorane, 3,6-dimethoxyfluorane, and 2,4-dimethyl-6-(4-dimethylaminophenyl)-aminofluorane may be cited.

As concrete examples of the near infrared absorption dye, 3-(4-(4-(4-anilino)-anilino)anilino-6-methyl-7-chlorofluorane, 3,3-bis(2-(4-dimethylaminophenyl)-2-(4-methoxyphenyl)vinyl)-4,5,6,7-tetrachlorophthalide, and 3,6,6'-tris(dimethylamino)-spiro[fluorene-9,3'-phthalide] may be cited. Besides, 3,3-bis(4'-diethylaminophenyl)-6-diethylaminophthalide may be cited.

As typical examples of the developer for the thermal printing paper which uses the compound or combination of this invention as a stabilizer of image conservation, optionally in combination with other developer, bisphenol compounds such as bisphenol A, 4,4'-sec-butylidene bisphenol, 4,4'-cyclohexylidene bisphenol, 2,2-dimethyl-3,3-bis(4-hydroxyphenyl)butane, 2,2'-dihydroxy diphenyl, pentamethylene-bis(4-hydroxy benzoate), 2,2-dimethyl-3,3-di(4-hydroxyphenyl)pentane, and 2,2-di(4-hydroxy-phenyl) hexane, sulfur-containing bisphenol compounds such as 4,4'-dihydroxydiphenyl thioether, 1,7-di(4-hydroxphenylthio)-3,5-dioxaheptane, 2,2'-bis(4-hydroxyphenylthio)diethyl ether, and 4,4'-dihydroxy-3,3'-dimethyldiphenyl thioether, 4-hydroxybenzoic esters such as benzyl 4-hydroxybenzoate, ethyl 4-hydroxybenzoate, propyl 4-hydroxybenzoate, isopropyl 4-hydroxybenzoate, butyl 4-hydroxybenzoate, isobutyl 4-hydroxybenzoate, chlorobenzyl 4-hydroxybenzoate, methylbenzyl 4-hydroxybenzoate, and diphenyl-methyl 4-hydroxybenzoate, metal salts of benzoic acid such as zinc benzoate and zinc 4-nitrobenzoate, salicylic acids such as 4-(2-(4-methoxyphenyloxy)ethyloxy)salicylic acid, metal salts of salicylic acid such as zinc salicylate and zinc bis[4-(octyloxycarbonylamino)-2-hydroxybenzoate], hydroxysulfones such as 4,4'-dihydroxydiphenyl sulfone, 2,4'-dihydroxydiphenyl sulfone, 4-hydroxy-4'-methyldiphenyl sulfone, 4-hydroxy-4'-isopropoxydiphenyl sulfone, 4-hydroxy-4'-butoxydiphenyl sulfone, 4,4'-dihydroxy-3,3'-diallyldiphenyl sulfone, 3,4-dihydroxy-4'-methyldiphenyl sulfone, and 4,4'-dihydroxy-3,3',5,5'-tetrabromo-diphenyl sulfone, 4-hydroxyphthalic diesters such as dimethyl 4-hydroxyphthalate, dicyclohexyl 4-hydroxyphthalate, and diphenyl 4-hydroxyphthalate, hydroxynaphthoeic esters such as 2-hydroxy-6-carboxynaphthalene, hydroxyacetophenone, p-phenylphenol, benzyl 4-hydroxyphenyl acetate, p-benzyl phenol, hydroquinone-monobenzyl ether, trihalomethyl sulfones such as tribromomethylphenyl sulfone, sulfonyl ureas such as 4,4'-bis(p-toluenesulfonylamino-carbonylamino) diphenyl methane, tetracyanoquinodimethanes, and 2,4-dihydroxy-2'-methoxybenzanilide may be cited.

As typical examples of the stabilizer of image conservation for the thermal printing paper which uses the compound or combination of this invention as a developer optionally in combination with other developer, epoxy group-containing diphenyl sulfones such as 4-benzyloxy-4'-(2-methylglycidyloxy)-diphenyl sulfone and 4,4'-diglycidyloxydiphenyl sulfone, 1,4-diglycidyl-oxybenzene, 4-(a-(hydroxymethyl)benzyloxy)-4'-hydroxydiphenyl sulfone, metal salts (particularly zinc salts) of 2-propanol derivatives, salicylic acid derivatives, and oxynaphtheic acid derivatives, metal salts of 2,2-methylene-bis(4,6-tert-butylphenyl)phosphate, and other water-insoluble zinc compounds may be cited.

As concrete examples of the sensitizer, higher fatty acid amides such as stearic acid amide, benzamide, stearic acid anilide, thioacetanilide, dibenzyl oxalate, di(4-methylbenzyl)oxalate, di(4-chlorobenzyl)oxalate, dimethyl phthalate, dimethyl terephthalate, dibenzyl terephthalate, dibenzyl isophthalate, bis(tert-butyl phenols), diphenyl sulfone and derivatives thereof, diesters of 4,4'-dihydroxydiphenyl sulfone, diethers of 2,4'-dihydroxydiphenyl sulfone, 1,2-bis(phenoxy)ethane, 1,2-bis(4-methylphenoxy)ethane, 1,2-bis(3-methylphenoxy) ethane, 2-naphthol benzyl ether, diphenyl amine, carbazole, 2,4-di-m-tolyl butane, 4-benzyl biphenyl, 1,4'-dimethyl biphenol, m-terphenyl, d-b-naphthylphenylene diamine, phenyl 1-hydroxynaphthoate, 2-naphthylbenzyl ether, 4-methylphenyl-biphenyl ether, 2,2-bis(3,4-dimethylphenyl)ethane, 2,3,5,6-tetramethyl-4'-methyldiphenyl methane, and diphenyl carbonate may be cited. Among other sensitizers mentioned above, ethers such as 1,2-bis(3-methyl-phenoxy)ethane and 2-naphthylbenzyl ether and arbenzyl biphenorbons such as m-terphenyl, 4-benzyl biphenol, and di(4-methylbenzyl)oxalate prove to be particularly preferable. More preferable examples are diphenyl sulfone and derivatives thereof, especially diethers of 4,4'-dihydroxydiphenyl sulfone and diethers of 2,4'-dihydroxydiphenyl sulfone. As concrete examples of these preferred compounds, 4,4'-dimethoxydiphenyl sulfone, 4,4'-diethoxydiphenyl sulfone, 4,4'-dipropoxydiphenyl sulfone, 4,4'-diisopropoxydiphenyl sulfone, 4,4'-dibutoxydiphenyl sulfone, 4,4'-diisobutoxydiphenyl sulfone, 4,4'-dipentyloxydiphenyl sulfone, 4,4'-dihexyloxydiphenyl sulfone, 2,4'-dimethoxydiphenyl sulfone, 2,4'-diethoxydiphenyl sulfone, 2,4'-dipropoxydiphenyl sulfone, 2,4'-diisopropoxydiphenyl sulfone, 2,4'-dibutoxydiphenyl sulfone, 2,4'-diisobutoxydiphenyl sulfone, 2,4'-dipentyloxydiphenyl sulfone, and 2,4'-dihexyloxydiphenyl sulfone may be cited.

The fillers which can be effectively used herein include silica, clay, kaoline, calcined kaoline, talc, satin white, aluminum hydroxide, calcium carbonate, magnesium carbonate, zinc oxide, titanium dioxide, barium sulfate, magnesium silicate, aluminum silicate, and plastic segment, for example. For the recording material of this invention, salts of alkaline earth metals prove to be particularly useful. Carbonates such as, for example, calcium carbonate and magnesium carbonate prove to be further preferable. The amount of the filler to be used is in the range of 0.1–15 parts by weight, preferably 1–10 parts by weight, based on one part by weight of the coloring dye. Optionally, the filler may be used as mixed with other filler.

As concrete examples of the dispersing agent, sulfosuccinic esters such as dioctyl sodium sulfosuccinate and sodium dodecylbenzene sulfonate, sodium salts of laurylalcohol sulfuric esters, and fatty acid salts may be cited.

As concrete examples of the antioxidant, 2,2'-methylenebis-(4-methyl-6-tert-butylphenol), 2,2'-methylenebis(4-ethyl-6-tert-butylphenol), 4,4'-propylmethylenebis(3-methyl-6-tert-butyl-phenol), 4,4'-butylidenebis(3-methyl-6-tert-butylphenol), 4,4'-thiobis(2-tert-butyl-5-methylphenol), 1,1,3-tris(2-methyl-4-hydroxy-5-tert-butylphenyl)butane, 1,1,3-tris(2-methyl-4-hydroxy-5-cyclohexylphenyl)butane, and 4-[4-[1,1-bis(4-hydroxy-phenyl)ethyl]-a,a-dimethylbenzyl)phenol may be cited.

The desensitizing agents which are effectively used herein include aliphatic higher alcohols, polyethylene glycol, and guanidine derivatives, for example.

The viscosity inhibitors which are effectively used herein include stearic acid, zinc stearate, calcium stearate, carnauba wax, paraffin wax, and ester wax, for example.

The light stabilizers which are effectively used herein include salicylic acid type ultraviolet absorbents such as phenyl salicylate, p-tert-butylphenyl salicylate, and p-octylphenyl salicylate, benzophenone type ultraviolet absorbents such as 2,4-dihydroxybenzophenone, 2-hydroxy-4-methoxybenzophenone, 2-hydroxy-4-benzyloxybenzophenone, 2-hydroxy-4-octylbenzophenone, 2-hydroxy-4-dodecyloxybenzophenone, 2,2'-dihydroxy-4-methoxy-benzophenone, 2,2'-dihydroxy-4,4'-dimethoxybenzophenone, 2-hydroxy-4-methoxy-5-sulfobenzophenone, and bis(2-methoxy-4-hydroxy-5-benzoylphenyl)methane, benzotriazole type ultraviolet absorbents such as 2-(2'-hydroxy-5'-methylphenyl) benzotriazole, 2-(2'-hydroxy-5'-tert-butylphenyl) benzotriazole, 2-(2'-hydroxy-3',5'-di-tert-butylphenyl) benzotriazole, 2-(2'-hydroxy-3'-tert-butyl-5'-methylphenyl)-5-chlorobenzotriazole, 2-(2'-hydroxy-3',5'-di-tert-butylphenyl)-5-chlorobenzotriazole, 2-(2'-hydroxy-3',5'-di-tert-amylphenyl)benzotriazole, 2-[2'-hydroxy-3'-(3",4",4",5",6"-tetrahydrophthalimidomethyl)-5'-methyl-phenyl] benzotriazole, 2-(2'-hydroxy-5'-tert-octylphenyl) benzotriazole, 2-[2'-hydroxy-3',5'-bis(a,a-dimethylbenzyl) phenyl]-2H -benzotriazole, 2-(2'-hydroxy-3'-dodecyl-5'-methylphenyl)benzo-triazole, 2-(2'-hydroxy-3'-undecyl-5'-methylphenyl)benzo-triazole, 2-(2'-hydroxy -3'-tridecyl-5'- methylphenyl)benzo-triazole, 2-(2'-hydroxy-3'-tetradecyl-5'-methylphenyl)benzo-triazole, 2-(2'-hydroxy-3'-pentadecyl-5'-methylphenyl)benzo-triazole, 2-(2'-hydroxy-3'-hexadecyl-5'-methylphenyl)benzo-triazole, 2-[2'-hydroxy-4'-(2"-ethylhexyl)oxyphenyl]benzo-triazole, 2-[2'-hydroxy-4'-(2"-ethylheptyl)oxyphenyl]benzo-triazole, 2-2-[2'-hydroxy-4'-(2"-ethyloctyl)oxyphenyl]benzo-triazole, 2-[2'-hydroxy-4'-(2"-propyloctyl)oxyphenyl]benzo-triazole, 2-[2'-hydroxy-4'-(2"-propylheptyl)oxyphenyl]benzo-triazole, 2-[2'-hydroxy-4'-(2"propylhexyl)oxyphenyl]benzo-triazole, 2-[2'-hydroxy-4'-(1"-ethylhexyl)oxyphenyl]benzo-triazole, 2-[2'-hydroxy-4'-(1"-ethylheptyl)oxyphenyl]benzo-triazole, 2-[2'-hydroxy-4'-(1'-ethyloctyl)oxyphenyl]benzo-triazole, 2-[2'-hydroxy-4'-(1"-propyloctyl)oxyphenyl]benzo-triazole, 2-[2'-hydroxy-4'-(1"-propylheptyl)oxyphenyl]benzo-triazole, 2-[2'-hydroxy-4'-(1"-propylhexyl)oxyphenyl]benzo-triazole, 2,2'-methylenebis [4-(1,1,3,3-tetramethylbutyl)-6-(2H-benzotriazol-2-yl)] phenol, and condensate of polyethylene glycol with methyl-3-[3-tert-butyl-5-(2H-benzotriazol-2-yl)-4-hydroxy-phenyl] propionate, cyanoacrylate type ultraviolet absorbents such as 2'-ethylhexyl-2-cyano-3,3-diphenyl acrylate and ethyl-2-cyano-3,3-diphenyl acrylate, hindered amine type ultraviolet absorbents such as bis(2,2,6,6-tetramethyl-4-piperidyl) sebacate, bis(2,2,6,6-tetramethyl-4-piperidyl)succinate, and bis(1,2,2,6,-6-pentamethyl-4-piperidyl)-2-(3,5-di-tert-butyl) malonate, and 1,8-dihydroxy-2-acetyl-3-methyl-6-methoxy naphthalene and related compound thereof, for example.

The following compounds may be cited as examples of the fluorine dye:

Disodium salt of 4,4'-bis[2-anilino-4-(2-hydroxyethyl) amino-1,3,5-triazinyl-6-amino]stilben-2,2'-disulfonic acid, disodium salt of 4,4'-bis[2-anilino-4-bis(hydroxyethyl) amino-1,3,5-triazinyl-6-amino]stilben-2,2'-disulfonic acid, disodium salt of 4,4'-bis[2-methoxy-4-(2-hydroxyethyl) amino-1,3,5-triazinyl-6-amino]stilben-2,2'-disulfonic acid, disodium salt of 4,4'-bis[2-methoxy-4-(2-hydroxypropyl) amino-1,3,5-triazinyl-6-amino]stilben-2,2'-disulfonic acid, disodium 4,4'-bis[2-m-sulfoanilino-4-bis-(hydroxyethyl) amino-1,3,5-triazinyl-6-amino]stilben-2,2'-disulfonic acid, tetrasodium salt of 4-[2-p-sulfoanilino-4 -bis(hydroxyethyl) amino-1,3,5-triazinyl-6-amino]-4'-[2-m-sulfo-anilino-4-bis (hydroxyethyl)amino-1,3,5-triazinyl-6-amino]stilben-2,2'-disulfonic acid, tetrasodium salt of 4,4'-bis[2-p-sulfo-anilino-4-bis(hydroxyethyl)amino-1,3,5-triazinyl-6-amino] stilben-2,2'-disulfonic acid, hexasodium salt of 4,4'-bis[2-(2,5-disulfo-anilino)-4-phenoxyamino-1,3,5-triazinyl-6-amino]stilben-1,1'-disulfonic acid, hexasodium salt of 4,4'-bis[2-(2,5-disulfo-anilino)-4-(p-methoxycarbonylphenoxy) amino-1,3,5-triazinyl-6-amino]stilben-2,2'-disulfonic acid, tetrasodium salt of 4,4'-bis[2-(p-sulfophenoxy)-4-bis (hydroxyethyl)amino-1,3,5-triazinyl-6-amino]stilben-2,2'-disulfonic acid, hexasodium salt of 4,4'-bis[2-(2,5-disulfoanilino)-4-formalinylamino-1,3,5-triazinyl-6-amino] stilben-2,2'-disulfonic acid, and hexasodium salt of 4,4'-bis [2-(2,5-disulfoanilino)-4-bis(hydroxyethyl)amino-1,3,5-triazinyl-6-amino]stilben-2,2'-disulfonic acid.

The compound or composition of this invention is used in the production of a thermal printing paper in the same manner as when a known stabilizer of image conservation, developer, or sensitizer is used. A coloring sheet, for example, is produced by microcapsulating a coloring dye by a known method, dispersing the produced microcapsules in a proper dispersing agent, and applying the resultant dispersion to a paper. A developing sheet is produced by applying the dispersion of a developing agent to paper. When the compound of this invention is used in this case as a stabilizer of image conservation, it may be used as dispersed in the dispersion used in either the coloring sheet or the developing sheet. The pressure-sensitive copying paper is manufactured by combining the two sheets prepared as described above.

The pressure-sensitive copying paper may be composed of an upper sheet having deposited on the lower side thereof such microcapsules as enclose a solution of a coloring dye in an organic solvent and a lower sheet having a developing agent (acidic substance) deposited on the upper side thereof. It may be otherwise a so-called self-content paper which has both microcapsules and developing agent applied on one and the same sheet of paper.

The developing agent to be used in this case or the developing agent to be used as mixed with the compound of this invention may be any of the heretofore known developing agents. As concrete examples of the developing agent, inorganic acidic substances such as acid clay, activated clay, attapulgite, bentonite, colloidal silica, aluminum silicate, magnesium silicate, zinc silicate, tin silicate, calcined kaoline, and talc, aliphatic carboxylic acids such as oxalic acid, maleic acid, tartaric acid, citric acid, succinic acid, and stearic acid, aromatic carboxylic acids such as benzoic acid, p-tert-butylbenzoic acid, phthalic acid, gallic acid, salicylic acid, 3-isopropyl salicylic acid, 3-phenyl salicylic acid, 3-cyclohexyl salicylic acid, 3,5-di-tert-butyl salicylic acid, 3-methyl-5-penzyl salicylic acid, 3-phenyl-5-(2,2-dimethylbenzyl)salicylic acid, 3,5-di-(2-methyl-benzyl) salicylic acid, and 2-hydroxy-1-benzyl-3-naphthoeic acid, zinc, magnesium, aluminum, titanium, and other metal salts of such aromatic carboxylic acids, phenol resin type developing agents such as p-phenylphenol-formalin resin and p-butylphenol-acetylene resin, and mixtures of such phenol resin type developing agent with the aromatic carboxylic acids mentioned above may be cited.

Now, the recording materials of the present invention will be described in detail below with reference to working examples. It should be noted, however, that this invention does not need to be limited to these examples.

EXAMPLE 11

| Dye dispersion (A solution) | |
| --- | --- |
| 2-Anilino-3-methyl-6-dibutylamino fluorane | 7.0 g |
| Aqueous 15% polyvinyl alcohol solution | 30.0 g |
| Filler (calcium carbonate) | 13.5 g |
| Purified water | 49.5 g |
| Dispersion of developing agent (B solution) | |
| Compound of this invention (Compound No. 1 of Example 1) | 7.0 g |
| Aqueous 15% polyvinyl alcohol solution | 30.0 g |
| Filler (calcium carbonate) | 13.5 g |
| Purified water | 49.5 g |
| Dispersion of filler (C solution) | |
| Aqueous 15% polyvinyl alcohol solution | 30.0 g |
| Filler (calcium carbonate) | 20.5 g |
| Purified water | 49.5 g |

The mixtures of the compositions shown above were severally attrited thoroughly with a sand grinder to prepare the dispersions of A solution, B solution, and C solution. A coating liquid was prepared by mixing one part by weight of A solution, two parts by weight of B solution, and one part by weight of C solution. A thermal printing paper was manufactured by applying the coating liquid to a sheet of white paper by the use of a wire rod (No. 12), drying the applied layer of the coating liquid on the paper, and thereafter subjecting the coated paper to a calendering treatment.

COMPARATIVE EXAMPLE 1

A thermal printing paper was manufactured by repeating the procedure of Example 11 while using 4-isopropoxy-4'-hydroxy-diphenyl sulfone in the place of the compound of this invention in the dispersion of the developing agent.

EXAMPLES 12–16

Thermal printing papers were manufactured by repeating the procedure of Example 11 while using 6-phenoxy-2,4-di [4-(4-hydroxyphenylsulfonyl)phenoxy]-1,3,5-triazine (compound No. 8 of Example 2), 2-anilino-4,6-di[4-(4-hydroxyphenylsulfonyl)phenoxy]-1,3,5-triazine (compound No. 24 of Example 3), 6-(4-hydroxy-phenyl)thio-2,4-di[4-(4-hydroxyphenylsulfonyl)phenoxy]-1,3,5-triazine (compound No. 19 of Example 4), 2-ethoxy-4,6-di[4-(4-hydroxyphenylsulfonyl)phenoxy]-1,3,5-triazine (compound No. 2), and 2-isopropoxy-4,6-di[4-(4-hydroxyphenylsulfonyl)phenoxy]-1,3,5-triazine (compound No. 4) respectively in the place of the compound 1 of this invention in the dispersion of developing agent.

EXAMPLE 17

A thermal printing paper was manufactured by repeating the procedure of Example 11 while using 6-phenoxy-2,4-di [4-(4-hydroxyphenylsulfonyl)phenoxy]-1,3,5-triazine (compound No. 8 of Example 2) in the place of the compound 1 of this invention in the dispersion of the developing agent and using a dispersion of filler (C solution) composed of 7.0 g of di(4-methylbenzyl)oxalate, 30.0 g of an aqueous 15% polyvinyl alcohol solution, 13.5 g of filler (clay), and 49.5 g of purified water instead.

EXAMPLE 18

Manufacture of Thermal Printing Paper

| Dispersion of dye (A solution) | |
|---|---|
| 2-Anilino-3-methyl-6-dibutylamino fluorane | 20.0 g |
| Aqueous 10% polyvinyl alcohol solution | 105.0 g |
| Dispersion of developing agent (B solution) | |
| 4,4'-bis[2-(4-hydpoxyphenylsulfonyl)phenoxy-4-methoxy-1, 3,5-triazin-6-yloxy]diphenyl sulfone (compound 2-1 of Example 5) | 20.0 g |
| Aqueous 10% polyvinyl alcohol solution | 105.0 g |
| Dispersion of sensitizer (C solution) | |
| Bis(4-methylbenzyl) oxalate | 20.0 g |
| Aqueous 10% polyvinyl alcohol solution | 105.0 g |
| Dispersion of filler (D solution) | |
| Aqueous 10% polyvinyl alcohol solution | 26.2 g |
| Filler (calcium carbonate) | 27.8 g |
| Purified water | 71.0 g |

The mixtures of the compositions shown above were severally attrited thoroughly with a sand grinder to prepare the dispersions of A solution, B solution, C solution, and D solution. A coating liquid was prepared by mixing one part by weight of A solution, two parts by weight of B solution, one part by weight of C solution, 4 parts by weight of D solution, and 0.5 part by weight of a dispersion of zinc stearate (made by Chukyo Yushi K.K. and sold under the trademark designation of "Hydrin Z-70-30""). A thermal printing paper was manufactured by applying the coating liquid to a sheet of white paper by the use of a wire rod (No. 12), drying the applied layer of the coating liquid on the paper, and thereafter subjecting the coated paper to a calendering treatment. (The amount of application was about 5.5 g/m$^2$ on dry basis.)

EXAMPLE 19

A thermal printing paper. was manufactured by repeating the procedure of Example 18 while using 4,4'-bis[2-(4-hydroxy-phenylsulfonyl)phenoxy-4-methylamino-1,3,5-triazin-6-yloxy]-diphenyl sulfone (Compound 2-12) in the place of the 4,4'-bis[2-(4-hydroxyphenylsulfonyl)phenoxy-4-methoxy-1,3,5-triazin-6-yloxy]-diphenyl sulfone in the B solution of Example 18.

EXAMPLE 20

A thermal printing paper was manufactured by repeating the procedure of Example 18 while using 4,4'-bis[4-(4-hydroxyphenylsulfonyl)phenoxy-2-dimethylamino-1,3,5-triazin-6-yloxy]diphenyl sulfone (Compound 2-16) in the place of the 4,4'-bis[2-(4-hydroxyphenylsulfonyl)phenoxy-4-methoxy-1,3,5-triazin-6-yloxy]-diphenyl sulfone in the B solution of Example 18.

EXAMPLE 21

A thermal printing paper was manufactured by repeating the procedure of Example 18 while using 4,4'-bis[2-(4-hydroxyphenylsulfonyl)phenoxy-4-methoxy-1,3,5-triazin-6-yloxy]-diphenyl sulfone in the place of the 4,4'-bis[2-(4-hydroxyphenyl-sulfonyl)phenoxy-4-methoxy-1,3,5-triazin-6-yloxy]-diphenyl sulfone in the B solution of Example 18.

EXAMPLE 22

A thermal printing paper was manufactured by repeating the procedure of Example 18 while using the composition produced in Example 7 in the place of the 4,4'-bis[2-(4-hydroxyphenyl-sulfonyl)phenoxy-4-methoxy-1,3,5-triazin-6-yloxy]-diphenyl sulfone in the B solution of Example 18.

EXAMPLE 23

A thermal printing paper was manufactured by repeating the procedure of Example 18 while using the composition produced in Example 8 in the place of the 4,4'-bis[2-(4-hydroxyphenyl-sulfonyl)phenoxy-4-methoxy-1,3,5-triazin-6-yloxy]-diphenyl sulfone in the B solution of Example 18.

EXAMPLE 24

A thermal printing paper was manufactured by repeating the procedure of Example 18 while using the composition produced in Example 9 in the place of the 4,4'-bis[2-(4-hydroxyphenyl-sulfonyl)phenoxy-4-methoxy-1,3,5-triazin-6-yloxy]-diphenyl sulfone in the B solution of Example 18.

EXAMPLE 25

A thermal printing paper was manufactured by repeating the procedure of Example 18 while using the composition produced in Example 10 in the place of the 4,4'-bis[2-(4-hydroxyphenyl-sulfonyl)phenoxy-4-methoxy-1,3,5-triazin-6-yloxy]-diphenyl sulfone in the B solution of Example 18.

COMPARATIVE EXAMPLE 2

A thermal printing paper was manufactured by repeating the procedure of Example 18 while using 4-isopropoxy-4'-hydroxydiphenyl sulfone in the place of the 4,4'-bis[2-(4-hydroxyphenyl-sulfonyl)phenoxy-4-methoxy-1,3,5-triazin-6-yloxy]-diphenyl sulfone in the B solution of Example 18.

TEST EXAMPLE 1

Test of Thermal Printing Paper for Resistance to Plasticizer

The thermal printing papers manufactured in Examples 11–25 and Comparative Examples 1 and 2 were caused to generate color in a checkerboard pattern by means of a thermal printing paper coloring tester (made by Okura Denki K.K. and sold under the product code of "TH-PMD") under the conditions of 26 V of printing voltage and 1.8 ms of pulse width and the colored faces of the thermal printing papers were coated intimately with a vinyl chloride wrap film. The samples thus prepared were left standing for 8 hours in an atmosphere kept at 40° C. to test for resistance to plasticizer. The samples were tested for color density before and after the test for resistance to plasticizer by means of a reflection density meter, McBath RD-514 (using a filter #106). The results are shown in Table 2.

The numerical values shown in Table 2 are such that the density of generated color increases in accordance as the numerical value increases. Those of the residual ratio are such that the degree of fading decreases in accordance as the numerical value increases.

TABLE 2

(Test for resistance to plasticizer)

| Example | Colored image (Before test) | Colored image (After test) | Residual ratio (%) |
|---|---|---|---|
| 11 Compound No. 1 | 0.97 | 0.82 | 85 |
| 12 Compound No. 8 | 0.96 | 0.89 | 93 |
| 13 Compound No. 24 | 0.98 | 0.86 | 88 |
| 14 Compound No. 19 | 0.94 | 0.89 | 95 |
| 15 Compound No. 2 | 1.03 | 0.87 | 84 |
| 16 Compound No. 4 | 1.00 | 0.93 | 93 |
| 17 Compound No. 8 | 1.12 | 0.82 | 73 |
| Comparative Example 1 | 1.17 | 0.07 | 6 |
| 18 Compound 2-1 | 0.95 | 0.91 | 96 |
| 19 Compound 2-12 | 1.08 | 1.05 | 97 |
| 20 Compound 2-16 | 1.10 | 1.08 | 98 |
| 21 | 1.14 | 0.86 | 75 |
| 22 | 1.12 | 1.10 | 98 |
| 23 | 1.07 | 1.06 | 99 |
| 24 | 1.11 | 1.08 | 97 |
| 25 | 1.06 | 1.05 | 99 |
| Comparative Example 2 | 1.16 | 0.08 | 7 |

Residual ratio = [Density of colored image (after test)] ÷ [Density of colored image (before test)] × 100

TEST EXAMPLE 2

Test of Thermal Printing Paper for Resistance to Oil

The thermal printing papers manufactured in Examples 18–25 and Comparative Example 2 were caused to generate color in the same manner as in Test Example 1 and the samples bearing a colored image were immersed in salad oil and then left standing therein at 25° C. for 24 hours to test for resistance to oil. The optical densities of the colored images were determined before and after the immersion in the oil by means of a reflection density meter, McBath RD-514 (using a filter #106). The results are shown in Table 3.

The numerical values shown in Table 3 are such that the density of generated color increases in accordance as the numerical value increases. Those of the residual ratio are such that the degree of fading decreases in accordance as the numerical value increases.

TABLE 3

(Test for resistance to oil)

| Example | Colored image (Before test) | Colored image (After test) | Residual ratio (%) |
|---|---|---|---|
| 18 Compound 2-1 | 0.95 | 0.94 | 99 |
| 19 Compound 2-12 | 1.08 | 1.02 | 94 |
| 20 Compound 2-16 | 1.10 | 1.05 | 95 |
| 21 | 1.17 | 1.09 | 92 |
| 22 | 1.12 | 1.09 | 97 |
| 23 | 1.07 | 1.06 | 99 |
| 24 | 1.11 | 1.10 | 99 |
| 25 | 1.06 | 1.05 | 99 |
| Comparative Example 2 | 1.16 | 1.12 | 14 |

INDUSTRIAL FEASIBILITY

The recording material which contains a triazine derivative of this invention exhibits outstanding stability to conserve a colored image and excels in resistance to oil and to plasticizer.

What is claimed is:

1. A triazine derivative represented by the general formula (I)

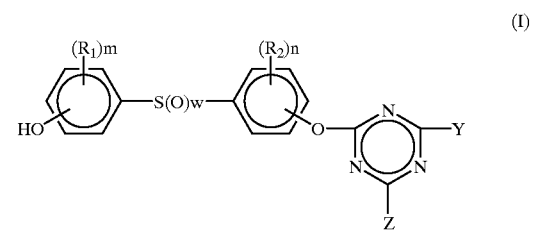

wherein $R_1$ and $R_2$, which may be the same or different, each represent a hydroxyl group, a halogen atom, a $C_1$–$C_6$ alkyl group, or a $C_2$–$C_4$ alkenyl group, n and m each represent an integer of 0–4, providing that where the integer is not less than 2, $R_1$ and $R_2$ may be different, w represents 0, 1, or 2, Y and Z, which may be the same or different, each represent

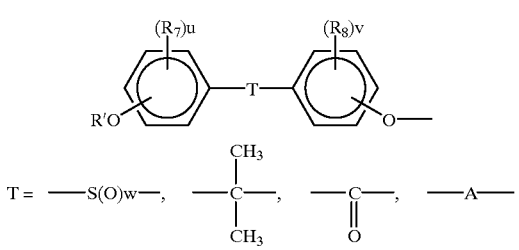

wherein R' represents a hydrogen atom or a $C_1$–$C_4$ alkyl group, $R_7$ and $R_8$, which may be same or different, each represent a hydroxyl group, a halogen atom, a $C_1$–$C_6$ alkyl group, a $C_2$–$C_4$ alkenyl group, u and v each represent an integer of 0–4, providing that where the integer is not less than 2, $R_7$ and $R_8$ may be different, w represent 0, 1, or 2, and A represents a $C_2$–$C_8$ alkylene group possessing an ether bond, or a halogen atom, a hydroxyl group, a hydrogen atom, a $C_1$–$C_6$ alkoxy group, a $C_1$–$C_6$ alkylthio group, an alkoxy group possessing an ether bond, an alkylthio group possessing an ether bond, an alkoxy group possessing a thioether bond, an alkylthio group possessing a thioether bond, a hydroxyalkoxy group, a hydroxyalkylthio group, a primary or secondary $C_1$–$C_6$ alkylamino group, a primary or secondary $C_1$–$C_6$ hydroxyalkylamino group, an aryloxy group optionally substituted with a hydroxyl group, a $C_1$–$C_4$ alkyl group, or a halogen atom, an arylthio group optionally substituted with a hydroxyl group, a $C_1$–$C_4$ alkyl group, or a halogen atom, an arylamino group optionally substituted with a hydroxyl group, a $C_1$–$C_4$ alkyl group, or a halogen atom, or an aralkyloxy group optionally substituted with a hydroxyl group, a $C_1$–$C_4$ alkyl group, or a halogen atom.

2. A triazine derivative represented by the general formula (II)

ondary $C_1$–$C_6$ alkylamino group, a primary or secondary $C_1$–$C_6$ hydroxyalkylamino group, an aryloxy group optionally substituted with a hydroxyl group, a $C_1$–$C_4$ alkyl group, or a halogen atom, an arylthio group optionally substituted with a hydroxyl group, a $C_1$–$C_4$ alkyl group, or a halogen atom, an arylamino group optionally substituted with a hydroxyl group, a $C_1$–$C_4$ alkyl group, or a halogen atom, or an aralkyloxy group optionally substituted with a hydroxyl group, a $C_1$–$C_4$ alkyl group, or a halogen atom.

3. A composition characterized by containing two or more triazine derivatives represented by the general formula (II)

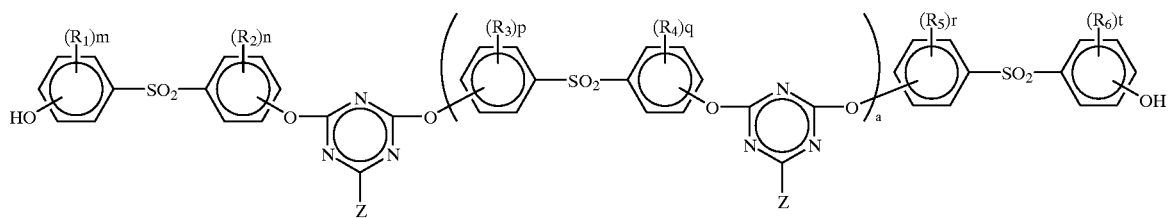

(II)

wherein $R_1$–$R_6$, which may be the same or different, each represent a hydroxyl group, a halogen atom, a $C_1$–$C_6$ alkyl group, or a $C_2$–$C_4$ alkenyl group, m, n, p, q, r, and t each

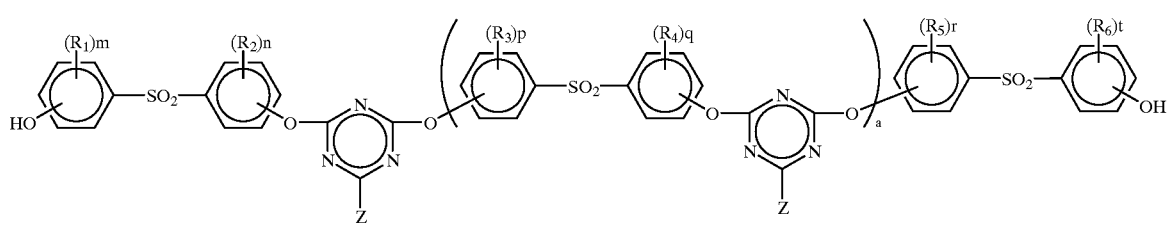

(II)

represent an integer of 0–4, providing that where the integer is not less than 2, $R_1$–$R_6$ may be different from one another, a represents an integer of 0–10, Z represents

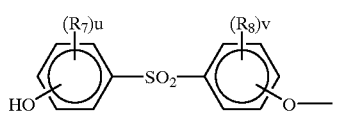

wherein $R_7$ and $R_8$, which may be the same or different, each represent a hydroxyl group, a halogen atom, a $C_1$–$C_6$ alkyl group, or a $C_2$–$C_4$ aklenyl group, and u and v each represent an integer of 0–4, providing that where the integer is not less than 2, $R_7$ and $R_8$ may be different from each other or a halogen atom, a hydroxyl group, a hydrogen atom, a $C_1$–$C_6$ alkoxy group, a $C_1$–$C_6$ alkylthio group, an alkoxy group possessing an ether bond, an alkylthio group possessing an ether bond, an alkoxy group possessing a thioether bond, an alkylthio group possessing a thioether bond, a hydroxyalkoxy group, a hydroxyalkylthio group, a primary or secwherein $R_1$–$R_6$, m, n, p, q, r, t, a, and Z have the same meanings as in claim 2.

4. A recording material containing a coloring dye, and at least one species of triazine derivative set forth in claim 2.

5. A recording material containing a coloring dye, and at least one species of composition set forth in claim 3.

6. A recording material containing a coloring dye and at least one species of triazine derivative represented by the general formula (I)

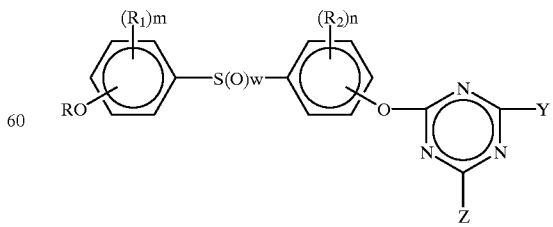

(I)

wherein R represents a hydrogen atom or a $C_1$–$C_4$ alkyl group, $R_1$ and $R_2$, which may be the same or different, each represent a hydroxyl group, a halogen atom, a $C_1$–$C_6$ alkyl group, or a $C_2$–$C_4$ alkenyl group, n and m each represent an integer of 0–4, providing that where the integer is not less than 2, $R_1$ and $R_2$ may be different, w represents 0, 1, or 2, Y and Z, which may be the same or different, each represent

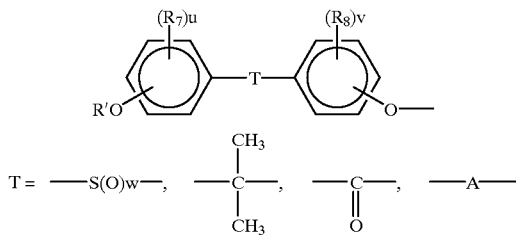

wherein R' represents a hydrogen atom or a $C_1$–$C_4$ alkyl group, $R_7$ and $R_8$, which may be the same or different, each represent a hydroxyl group, a halogen atom, a $C_1$–$C_6$ alkyl group, a $C_2$–$C_4$ alkenyl group, u and v each represent an integer of 0–4, providing that where the integer is not less than 2, $R_7$ and $R_8$ may be different, w represent 0, 1, or 2, and A represents a $C_2$–$C_8$ alkylene group possessing an ether bond, or a halogen atom, a hydroxyl group, a hydrogen atom, a $C_1$–$C_6$ alkoxy group, a $C_1$–$C_6$ alkylthio group, an alkoxy group possessing an ether bond, an alkylthio group possessing an ether bond, an alkoxy group possessing a thioether bond, an alkylthio group possessing a thioether bond, a hydroxyalkoxy group, a hydroxyalkylthio group, a primary or secondary $C_1$–$C_6$ alkylamino group, a primary or secondary $C_1$–$C_6$ hydroxyalkylamino group, an aryloxy group optionally substituted with a hydroxyl group, a $C_1$–$C_4$ alkyl group, or a halogen atom, an arylthio group optionally substituted with a hydroxyl group, a $C_1$–$C_4$ alkyl group, or a halogen atom, an arylamino group optionally substituted with a hydroxyl group, a $C_1$–$C_4$ alkyl group, or a halogen atom, or an aralkyloxy group optionally substituted with a hydroxyl group, a $C_1$–$C_4$ alkly group, or a halogen atom.

* * * * *

UNITED STATES PATENT AND TRADEMARK OFFICE
CERTIFICATE OF CORRECTION

PATENT NO : 6,143,060

DATED : November 7, 2000

INVENTOR(S) : Hiroshi Fujii, et al.

It is certified that error appears in the above-identified patent and that said Letters Patent are hereby corrected as shown below:

In the Formulas, Column 8
   replace

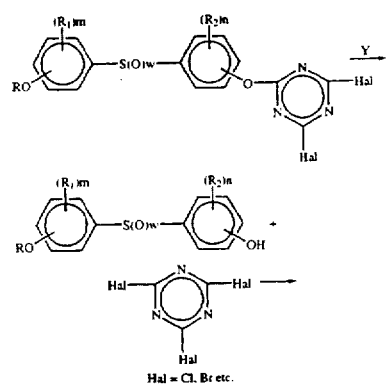

with

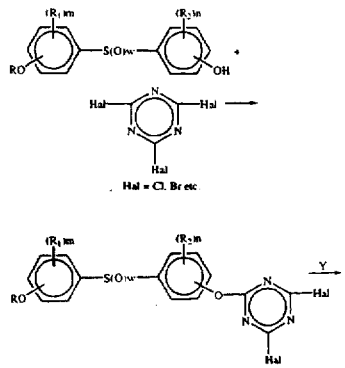

UNITED STATES PATENT AND TRADEMARK OFFICE
CERTIFICATE OF CORRECTION

PATENT NO : 6,143,060
DATED : November 7, 2000
INVENTOR(S) : Hiroshi Fujii, et al.

It is certified that error appears in the above-identified patent and that said Letters Patent are hereby corrected as shown below:

On title page, item 75 Inventors
 replace "Ichihara"
 with --Chiba--.

Signed and Sealed this

Eighth Day of May, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 6,143,060
DATED : November 7, 2000
INVENTOR(S) : Hiroshi Fujii, et al.

It is certified that error appears in the above-identified patent and that said Letters Patent is hereby corrected as shown below:

In table 1 Compund No. 81 (Column 26) replace

With 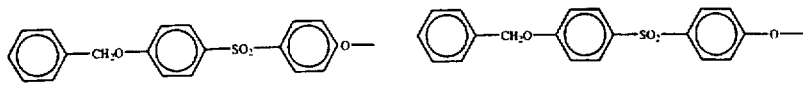

In table 1 Compound No. 89 (Column 27) replace

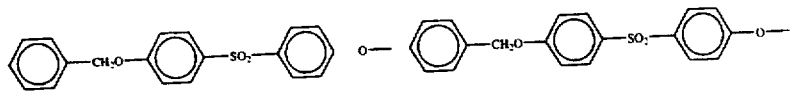

With 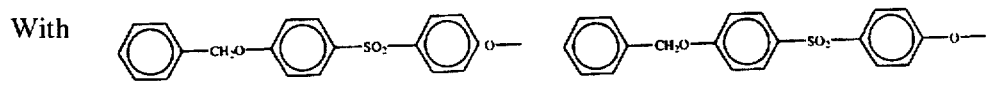

In table 1 Compund No. 109 (column 31) replace

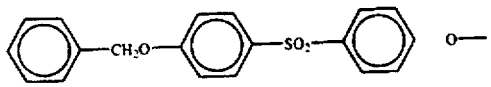

with 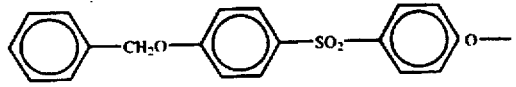

Signed and Sealed this

Second Day of October, 2001

Attest:

*Nicholas P. Godici*

NICHOLAS P. GODICI
*Attesting Officer*    *Acting Director of the United States Patent and Trademark Office*